(12) United States Patent
Gefen et al.

(10) Patent No.: US 8,428,740 B2
(45) Date of Patent: Apr. 23, 2013

(54) RETINAL PROSTHESIS TECHNIQUES

(75) Inventors: Ra'anan Gefen, Reut (IL); Tuvia Liran, Qiryal Tivon (IL)

(73) Assignee: Nano-Retina, Inc., Wilmington, DE (US)

( * ) Notice: Subject to any disclaimer, the term of this patent is extended or adjusted under 35 U.S.C. 154(b) by 201 days.

(21) Appl. No.: 12/852,218

(22) Filed: Aug. 6, 2010

(65) Prior Publication Data

US 2012/0035725 A1 Feb. 9, 2012

(51) Int. Cl.
*A61N 1/36046* (2006.01)

(52) U.S. Cl.
USPC .............................. 607/54; 607/53; 623/6.63

(58) Field of Classification Search .................... 607/54, 607/53; 623/6.63
See application file for complete search history.

(56) References Cited

U.S. PATENT DOCUMENTS

| | | | |
|---|---|---|---|
| 1,662,446 A | 3/1928 | Wappler | |
| 2,721,316 A | 10/1955 | Shaw | |
| 2,760,483 A | 8/1956 | Edward | |
| 4,272,910 A | 6/1981 | Danz | |
| 4,551,149 A | 11/1985 | Sciarra | |
| 4,601,545 A | 7/1986 | Kern | |
| 4,628,933 A * | 12/1986 | Michelson | 607/53 |
| 4,664,117 A | 5/1987 | Beck | |
| 4,786,818 A | 11/1988 | Mead et al. | |
| 4,837,049 A | 6/1989 | Byers et al. | |
| 4,903,702 A | 2/1990 | Putz | |
| 4,914,738 A | 4/1990 | Oda et al. | |
| 4,969,468 A | 11/1990 | Byers et al. | |
| 5,016,633 A | 5/1991 | Chow | |
| 5,024,223 A | 6/1991 | Chow | |
| 5,081,378 A | 1/1992 | Watanabe | |
| 5,108,427 A | 4/1992 | Majercik et al. | |
| 5,109,844 A | 5/1992 | de Juan, Jr. et al. | |

(Continued)

FOREIGN PATENT DOCUMENTS

| | | |
|---|---|---|
| WO | WO-0191854 A1 | 12/2001 |
| WO | WO-03032946 A2 | 4/2003 |

(Continued)

OTHER PUBLICATIONS

Delbrubk et al.: "Analog VLSI Adaptive, Logarithmic, wide-dynamic-Range Photoreceptor," 1994 International Symposium on Circuits and Systems (London, 1994), p. 339-342.

(Continued)

*Primary Examiner* — Christopher D Koharski
*Assistant Examiner* — Michael Carey
(74) *Attorney, Agent, or Firm* — Edwards Wildman Palmer LLP

(57) ABSTRACT

Apparatus is provided including an external device including, a mount, which is placed in front of an eye of a subject. A power source is coupled to the mount and emits energy toward the eye. An intraocular device is implanted entirely in the subject's eye, and includes a control unit, a plurality of stimulating electrodes, and an energy receiver, which receives the energy from the power source and generates a voltage drop in response. A plurality of photosensors detect photons and generate a signal in response. Driving circuitry is coupled to the energy receiver and to the photosensors, and drives the electrodes to apply electrical charges to a retina in response to the signals from the photosensors. The external device modulates the emitted energy, and the control unit demodulates the modulated energy to regulate an operation parameter of the intraocular device. Other embodiments are also described.

19 Claims, 13 Drawing Sheets

U.S. PATENT DOCUMENTS

| | | | |
|---|---|---|---|
| 5,133,356 | A | 7/1992 | Bryan et al. |
| 5,147,284 | A | 9/1992 | Fedorov et al. |
| 5,159,927 | A | 11/1992 | Schmid |
| 5,215,088 | A | 6/1993 | Normann et al. |
| 5,397,350 | A | 3/1995 | Chow et al. |
| 5,411,540 | A | 5/1995 | Edell et al. |
| 5,476,494 | A | 12/1995 | Edell et al. |
| 5,526,423 | A | 6/1996 | Ohuchi et al. |
| 5,575,813 | A | 11/1996 | Edell et al. |
| 5,597,381 | A | 1/1997 | Rizzo, III |
| 5,608,204 | A | 3/1997 | Hofflinger et al. |
| 5,674,263 | A | 10/1997 | Yamamoto et al. |
| 5,769,875 | A | 6/1998 | Peckham et al. |
| 5,800,478 | A | 9/1998 | Chen et al. |
| 5,800,533 | A | 9/1998 | Eggleston et al. |
| 5,800,535 | A | 9/1998 | Howard, III |
| 5,835,250 | A | 11/1998 | Kanesaka |
| 5,836,996 | A | 11/1998 | Doorish |
| 5,837,995 | A | 11/1998 | Chow et al. |
| 5,865,839 | A | 2/1999 | Doorish |
| 5,873,901 | A | 2/1999 | Wu et al. |
| 5,895,415 | A | 4/1999 | Chow et al. |
| 5,935,155 | A | 8/1999 | Humayun et al. |
| 5,944,747 | A | 8/1999 | Greenberg et al. |
| 5,949,064 | A | 9/1999 | Chow et al. |
| 6,020,593 | A | 2/2000 | Chow et al. |
| 6,032,062 | A | 2/2000 | Nisch |
| 6,035,236 | A | 3/2000 | Jarding et al. |
| 6,043,437 | A | 3/2000 | Schulman et al. |
| 6,069,365 | A | 5/2000 | Chow et al. |
| 6,075,251 | A | 6/2000 | Chow et al. |
| 6,201,234 | B1 | 3/2001 | Chow et al. |
| 6,230,057 | B1 | 5/2001 | Chow et al. |
| 6,259,937 | B1 | 7/2001 | Schulman et al. |
| 6,287,372 | B1 | 9/2001 | Briand et al. |
| 6,298,270 | B1 | 10/2001 | Nisch et al. |
| 6,324,429 | B1 | 11/2001 | Shire et al. |
| 6,347,250 | B1 | 2/2002 | Nisch et al. |
| 6,368,349 | B1 | 4/2002 | Wyatt et al. |
| 6,389,317 | B1 | 5/2002 | Chow et al. |
| 6,400,989 | B1 | 6/2002 | Eckmiller |
| 6,427,087 | B1 | 7/2002 | Chow et al. |
| 6,442,431 | B1 | 8/2002 | Veraart et al. |
| 6,458,157 | B1 * | 10/2002 | Suaning ............. 623/6.63 |
| 6,472,122 | B1 | 10/2002 | Schulman et al. |
| 6,473,365 | B2 | 10/2002 | Joh et al. |
| 6,498,043 | B1 | 12/2002 | Schulman et al. |
| 6,507,758 | B1 | 1/2003 | Greenberg et al. |
| 6,533,798 | B2 | 3/2003 | Greenberg et al. |
| 6,574,022 | B2 | 6/2003 | Chow et al. |
| 6,611,716 | B2 | 8/2003 | Chow et al. |
| 6,647,297 | B2 | 11/2003 | Scribner |
| 6,658,299 | B1 | 12/2003 | Dobelle |
| 6,677,225 | B1 | 1/2004 | Ellis et al. |
| 6,678,458 | B2 | 1/2004 | Ellis et al. |
| 6,683,645 | B1 | 1/2004 | Collins et al. |
| 6,738,672 | B2 | 5/2004 | Schulman et al. |
| 6,755,530 | B1 | 6/2004 | Loftus et al. |
| 6,758,823 | B2 | 7/2004 | Pasquale et al. |
| 6,761,724 | B1 | 7/2004 | Zrenner et al. |
| 6,762,116 | B1 | 7/2004 | Skidmore |
| 6,770,521 | B2 | 8/2004 | Visokay et al. |
| 6,785,303 | B1 | 8/2004 | Holzwarth et al. |
| 6,792,314 | B2 | 9/2004 | Byers et al. |
| 6,804,560 | B2 | 10/2004 | Nisch et al. |
| 6,821,154 | B1 | 11/2004 | Canfield et al. |
| 6,844,023 | B2 | 1/2005 | Schulman et al. |
| 6,847,847 | B2 | 1/2005 | Nisch et al. |
| 6,888,571 | B1 | 5/2005 | Koshizuka et al. |
| 6,904,239 | B2 | 6/2005 | Chow et al. |
| 6,908,470 | B2 | 6/2005 | Stieglitz et al. |
| 6,923,669 | B1 | 8/2005 | Tsui et al. |
| 6,935,897 | B2 | 8/2005 | Canfield et al. |
| 6,949,763 | B2 | 9/2005 | Ovadia et al. |
| 6,961,619 | B2 | 11/2005 | Casey |
| 6,970,745 | B2 | 11/2005 | Scribner |
| 6,974,533 | B2 | 12/2005 | Zhou |
| 6,976,998 | B2 | 12/2005 | Rizzo et al. |
| 6,990,377 | B2 | 1/2006 | Gliner et al. |
| 7,001,608 | B2 | 2/2006 | Fishman et al. |
| 7,003,354 | B2 | 2/2006 | Chow et al. |
| 7,006,873 | B2 | 2/2006 | Chow et al. |
| 7,025,619 | B2 | 4/2006 | Tsui et al. |
| 7,027,874 | B1 | 4/2006 | Sawan et al. |
| 7,031,776 | B2 | 4/2006 | Chow et al. |
| 7,035,692 | B1 | 4/2006 | Maghribi et al. |
| 7,037,943 | B2 | 5/2006 | Peyman |
| 7,047,080 | B2 | 5/2006 | Palanker et al. |
| 7,058,455 | B2 | 6/2006 | Huie, Jr. et al. |
| 7,071,546 | B2 | 7/2006 | Fey et al. |
| 7,079,881 | B2 | 7/2006 | Schulman et al. |
| 7,081,630 | B2 | 7/2006 | Saini et al. |
| 7,096,568 | B1 | 8/2006 | Nilsen et al. |
| 7,103,416 | B2 | 9/2006 | Ok et al. |
| 7,107,097 | B2 | 9/2006 | Stern et al. |
| 7,127,286 | B2 | 10/2006 | Mech et al. |
| 7,127,301 | B1 | 10/2006 | Okandan et al. |
| 7,130,693 | B1 | 10/2006 | Montalbo |
| 7,133,724 | B2 | 11/2006 | Greenberg et al. |
| 7,139,612 | B2 * | 11/2006 | Chow et al. ............. 607/53 |
| 7,147,865 | B2 | 12/2006 | Fishman et al. |
| 7,149,586 | B2 | 12/2006 | Greenberg et al. |
| 7,158,834 | B2 | 1/2007 | Paul, Jr. |
| 7,158,836 | B2 | 1/2007 | Suzuki |
| 7,160,672 | B2 | 1/2007 | Schulman et al. |
| 7,162,308 | B2 | 1/2007 | O'Brien et al. |
| 7,177,697 | B2 | 2/2007 | Eckmiller et al. |
| 7,190,051 | B2 | 3/2007 | Mech et al. |
| 7,191,010 | B2 | 3/2007 | Ohta et al. |
| 7,224,300 | B2 | 5/2007 | Dai et al. |
| 7,224,301 | B2 | 5/2007 | Dai et al. |
| 7,235,350 | B2 | 6/2007 | Schulman et al. |
| 7,242,597 | B2 | 7/2007 | Shodo |
| 7,244,027 | B2 | 7/2007 | Sumiya |
| 7,248,928 | B2 | 7/2007 | Yagi |
| 7,251,528 | B2 | 7/2007 | Harold |
| 7,255,871 | B2 | 8/2007 | Huie, Jr. et al. |
| 7,257,446 | B2 | 8/2007 | Greenberg et al. |
| 7,263,403 | B2 | 8/2007 | Greenberg et al. |
| 7,271,525 | B2 | 9/2007 | Byers et al. |
| 7,272,447 | B2 | 9/2007 | Stett et al. |
| 7,291,540 | B2 | 11/2007 | Mech et al. |
| 7,295,872 | B2 | 11/2007 | Kelly et al. |
| 7,302,598 | B2 | 11/2007 | Suzuki et al. |
| 7,314,474 | B1 | 1/2008 | Greenberg et al. |
| 7,321,796 | B2 | 1/2008 | Fink et al. |
| 7,342,427 | B1 | 3/2008 | Fensore et al. |
| 7,377,646 | B2 | 5/2008 | Suzuki |
| 7,379,000 | B2 | 5/2008 | Dai et al. |
| 7,388,288 | B2 | 6/2008 | Solzbacher et al. |
| 7,400,021 | B2 * | 7/2008 | Wu et al. ............. 257/414 |
| 7,447,547 | B2 | 11/2008 | Palanker |
| 7,447,548 | B2 | 11/2008 | Eckmiller |
| 7,480,988 | B2 | 1/2009 | Ok et al. |
| 7,481,912 | B2 | 1/2009 | Stelzle et al. |
| 7,482,957 | B2 | 1/2009 | Dai et al. |
| 7,483,751 | B2 | 1/2009 | Greenberg et al. |
| 7,493,169 | B2 | 2/2009 | Greenberg et al. |
| 7,499,754 | B2 | 3/2009 | Greenberg et al. |
| 7,539,544 | B2 | 5/2009 | Greenberg et al. |
| 7,555,328 | B2 | 6/2009 | Schulman et al. |
| 7,556,621 | B2 | 7/2009 | Palanker et al. |
| 7,565,202 | B2 | 7/2009 | Greenberg et al. |
| 7,565,203 | B2 | 7/2009 | Greenberg et al. |
| 7,571,004 | B2 | 8/2009 | Roy et al. |
| 7,571,011 | B2 | 8/2009 | Zhou et al. |
| 7,574,263 | B2 | 8/2009 | Greenberg et al. |
| 7,610,098 | B2 | 10/2009 | McLean |
| 7,622,702 | B2 | 11/2009 | Wu et al. |
| 7,630,771 | B2 | 12/2009 | Cauller |
| 7,631,424 | B2 | 12/2009 | Greenberg et al. |
| 7,638,032 | B2 | 12/2009 | Zhou et al. |
| 7,666,523 | B2 | 2/2010 | Zhou |
| 7,676,274 | B2 | 3/2010 | Hung et al. |
| 7,691,252 | B2 | 4/2010 | Zhou et al. |
| 7,706,887 | B2 | 4/2010 | Tai et al. |
| 7,706,893 | B2 | 4/2010 | Hung et al. |

| | | |
|---|---|---|
| 7,709,961 B2 | 5/2010 | Greenberg et al. |
| 7,725,191 B2 | 5/2010 | Greenberg et al. |
| 7,734,352 B2 | 6/2010 | Greenberg et al. |
| 7,738,962 B2 | 6/2010 | Greenberg et al. |
| 7,749,608 B2 | 7/2010 | Laude et al. |
| 7,750,076 B2 | 7/2010 | Laude et al. |
| 7,751,896 B2 | 7/2010 | Graf et al. |
| 7,765,009 B2 | 7/2010 | Greenberg et al. |
| 7,766,903 B2 | 8/2010 | Blumenkranz et al. |
| 7,776,197 B2 | 8/2010 | Zhou |
| 7,831,309 B1 | 11/2010 | Humayun et al. |
| 7,834,767 B2 | 11/2010 | Shodo |
| 7,835,798 B2 | 11/2010 | Greenberg et al. |
| 7,840,273 B2 | 11/2010 | Schmid |
| 7,846,285 B2 | 12/2010 | Zhou et al. |
| 7,853,330 B2 | 12/2010 | Bradley et al. |
| 7,871,707 B2 | 1/2011 | Laude et al. |
| 7,877,866 B1 | 2/2011 | Greenberg et al. |
| 7,881,799 B2 | 2/2011 | Greenberg et al. |
| 7,887,681 B2 | 2/2011 | Zhou |
| 7,894,909 B2 | 2/2011 | Greenberg et al. |
| 7,894,911 B2 | 2/2011 | Greenberg et al. |
| 7,904,148 B2 | 3/2011 | Greenberg et al. |
| 7,908,011 B2 | 3/2011 | McMahon et al. |
| 7,912,556 B2 | 3/2011 | Greenberg et al. |
| 7,914,842 B1 | 3/2011 | Greenberg et al. |
| 7,937,153 B2 | 5/2011 | Zhou et al. |
| 7,957,811 B2 | 6/2011 | Caspi et al. |
| 7,962,221 B2 | 6/2011 | Greenberg et al. |
| 7,979,134 B2 | 7/2011 | Chow et al. |
| 7,989,080 B2 | 8/2011 | Greenberg et al. |
| 8,000,804 B1 | 8/2011 | Wessendorf et al. |
| 8,010,202 B2 | 8/2011 | Shah et al. |
| 8,010,206 B2 | 8/2011 | Dai et al. |
| 8,014,868 B2 | 9/2011 | Greenberg et al. |
| 8,014,869 B2 | 9/2011 | Greenberg et al. |
| 8,014,878 B2 | 9/2011 | Greenberg et al. |
| 8,024,022 B2 | 9/2011 | Schulman et al. |
| 8,034,229 B2 | 10/2011 | Zhou et al. |
| 8,046,078 B2 | 10/2011 | Greenberg et al. |
| 8,060,211 B2 | 11/2011 | Greenberg et al. |
| 8,060,216 B2 | 11/2011 | Greenberg et al. |
| 8,068,913 B2 | 11/2011 | Greenberg et al. |
| 8,078,284 B2 | 12/2011 | Greenberg et al. |
| 8,090,447 B2 | 1/2012 | Tano et al. |
| 8,090,448 B2 | 1/2012 | Greenberg et al. |
| 8,103,352 B2 | 1/2012 | Fried et al. |
| 8,121,697 B2 | 2/2012 | Greenberg et al. |
| 8,131,375 B2 | 3/2012 | Greenberg et al. |
| 8,131,378 B2 | 3/2012 | Greenberg et al. |
| 8,145,322 B1 | 3/2012 | Yao et al. |
| 8,150,526 B2 | 4/2012 | Gross et al. |
| 8,150,534 B2 | 4/2012 | Greenberg et al. |
| 8,160,713 B2 | 4/2012 | Greenberg et al. |
| 8,165,680 B2 | 4/2012 | Greenberg et al. |
| 8,170,676 B2 | 5/2012 | Greenberg et al. |
| 8,170,682 B2 | 5/2012 | Greenberg et al. |
| 8,180,453 B2 | 5/2012 | Greenberg et al. |
| 8,180,454 B2 | 5/2012 | Greenberg et al. |
| 8,180,460 B2 | 5/2012 | Nevsmith et al. |
| 8,190,267 B2 | 5/2012 | Greenberg et al. |
| 8,195,266 B2 | 6/2012 | Whalen, III et al. |
| 8,197,539 B2 | 6/2012 | Nasiatka et al. |
| 8,200,338 B2 | 6/2012 | Grennberg et al. |
| 8,226,661 B2 | 7/2012 | Balling et al. |
| 8,239,034 B2 | 8/2012 | Greenberg et al. |
| 8,244,362 B2 | 8/2012 | Yonezawa |
| 8,249,716 B2 | 8/2012 | Tano et al. |
| 2002/0091421 A1 | 7/2002 | Greenberg et al. |
| 2003/0023297 A1 | 1/2003 | Byers et al. |
| 2003/0032946 A1 | 2/2003 | Fishman et al. |
| 2003/0132946 A1 | 7/2003 | Gold |
| 2004/0054407 A1 | 3/2004 | Tashiro et al. |
| 2004/0078064 A1 | 4/2004 | Suzuki |
| 2004/0088026 A1 | 5/2004 | Chow et al. |
| 2004/0098067 A1 | 5/2004 | Ohta et al. |
| 2004/0181265 A1 | 9/2004 | Palanker et al. |
| 2004/0189940 A1 | 9/2004 | Kutschbach et al. |
| 2005/0015120 A1 | 1/2005 | Seibel et al. |
| 2005/0119605 A1 | 6/2005 | Sohn |
| 2005/0146954 A1 | 7/2005 | Win et al. |
| 2006/0106432 A1 | 5/2006 | Sawan et al. |
| 2006/0111757 A9 | 5/2006 | Greenberg et al. |
| 2006/0184245 A1* | 8/2006 | Graf et al. .................. 623/6.63 |
| 2006/0282128 A1 | 12/2006 | Tai et al. |
| 2006/0287688 A1 | 12/2006 | Yonezawa |
| 2007/0005116 A1 | 1/2007 | Lo |
| 2007/0123766 A1 | 5/2007 | Whalen et al. |
| 2007/0142877 A1 | 6/2007 | McLean |
| 2007/0142878 A1 | 6/2007 | Krulevitch et al. |
| 2007/0191909 A1 | 8/2007 | Ameri et al. |
| 2008/0114230 A1 | 5/2008 | Addis |
| 2008/0234791 A1* | 9/2008 | Arle et al. .................. 607/117 |
| 2008/0262571 A1 | 10/2008 | Greenberg et al. |
| 2008/0288036 A1 | 11/2008 | Greenberg et al. |
| 2009/0002034 A1 | 1/2009 | Westendorp et al. |
| 2009/0005835 A1 | 1/2009 | Greenberg et al. |
| 2009/0024182 A1 | 1/2009 | Zhang et al. |
| 2009/0118805 A1 | 5/2009 | Greenberg et al. |
| 2009/0192571 A1 | 7/2009 | Stett et al. |
| 2009/0204207 A1 | 8/2009 | Blum et al. |
| 2009/0204212 A1 | 8/2009 | Greenberg et al. |
| 2009/0216295 A1 | 8/2009 | Zrenner et al. |
| 2009/0228069 A1 | 9/2009 | Dai et al. |
| 2009/0287275 A1 | 11/2009 | Suaning et al. |
| 2009/0326623 A1 | 12/2009 | Greenberg et al. |
| 2010/0174224 A1 | 7/2010 | Sohn |
| 2010/0204754 A1 | 8/2010 | Gross et al. |
| 2010/0249878 A1 | 9/2010 | McMahon et al. |
| 2010/0331682 A1 | 12/2010 | Stein et al. |
| 2011/0054583 A1 | 3/2011 | Litt et al. |
| 2011/0172736 A1 | 7/2011 | Gefen et al. |
| 2012/0035725 A1 | 2/2012 | Gefen et al. |
| 2012/0035726 A1 | 2/2012 | Gross et al. |
| 2012/0041514 A1 | 2/2012 | Gross et al. |
| 2012/0209350 A1 | 8/2012 | Taylor et al. |
| 2012/0221103 A1 | 8/2012 | Liran et al. |
| 2012/0259410 A1 | 10/2012 | Gefen et al. |

FOREIGN PATENT DOCUMENTS

| | | |
|---|---|---|
| WO | WO-2007009539 A2 | 1/2007 |
| WO | WO-2007/095395 A2 | 8/2007 |
| WO | WO-2010035173 A1 | 4/2010 |
| WO | WO-2010089739 A2 | 8/2010 |
| WO | WO-2011/086545 A2 | 7/2011 |
| WO | WO-2011086545 A2 | 7/2011 |
| WO | WO-2012/017426 A1 | 2/2012 |
| WO | WO-2012/114327 A2 | 8/2012 |
| WO | WO-2012/153325 A2 | 11/2012 |

OTHER PUBLICATIONS

An Office Action dated Aug. 24, 2011 issued during the prosecution of Applicant's U.S. Appl. No. 12/368,150.

An International Search Report and Written Opinion dated Aug. 12, 2011 issued during the prosecution of Applicant's International Application No. PCT/IL2011/00022.

International Search Report and Written Opinion dated Dec. 12, 2011 issued on International Application No. PCT/IL2011/00609.

U.S. Appl. No. 12/687,509, Gefen.

Zrenner E., 2002. "Will retinal implants restore vision?" Science 295(5557), pp. 1022-1025.

Jourdain R P., et al., "Fabrication of piezoelectric thick-film bimorph micro-actuators from bulk ceramics using batch-scale methods" Multi-Material Micro Manufacture, S. Dimov and W. Menz (Eds.) 2008 Cardiff University, Cardiff, UK., Whittles Publishing Ltd.

Lianga C, et al., "Surface modification of cp-Ti using femtosecond laser micromachining and the deposition of Ca/P layer" Materials Letters vol. 62, Issue 23, Aug. 31, 2008, pp. 3783-3786—an abstract.

Seo J M., et al., "Biocompatibility of polyimide microelectrode array for retinal stimulation," Materials Science and Engineering: C, vol. 24, No. 1, Jan. 5, 2004, pp. 185-189(5).

Sorkin R., et al., "Process entanglement as a neuronal anchorage mechanism to rough surfaces," Nanotechnology 20 (2009) 015101 (8pp).

Vorobyeva A Y. et al., "Metallic light absorbers produced by femtosecond laser pulses," Advances in Mechanical Engineering vol. 2010, Article ID 452749, 4 pages doi:10.1155/2010/452749, Hindawi Publishing Corporation.

Vorobyeva A Y. et al., "Femtosecond laser structuring of titanium implants," Applied Surface Science vol. 253, Issue 17, Jun. 30, 2007, pp. 7272-7280—an abstract.

Wallman L., et al., "The geometric design of micromachined silicon sieve electrodes influences functional nerve regeneration," Biomaterials May 2001:22(10):1187-93, (an abstract).

Warren M. Grill, et al. "Implanted Neural Interfaces: Biochallenges and Engineered Solutions", Annu. Rev. Biomed. Eng. 2009, 11:1.

Grill W., et al., "Implanted Neural Interfaces: Biochallenges and Engineered Solutions", Annu. Rev. Biomed. Eng. 2009. 11:1-2—an abstract.

An International Search Report dated Aug. 17, 2010, which issued during the prosecution of Applicant's PCT/IL10/00097.

Kim B., "Through-Silicon-Via Copper Deposition for Vertical Chip Integration" Master. Res. Soc. Symp. Proc. vol. 970, 2007 Material Research Society.

Puech M., et al., "Fabrication of 3D packaging TSV using DRIE" ALCATEL Micro Machining Systems, www.adixen.com 2007.

Stein DJ, et al., "High voltage with Si series photovoltaics" Proceedings of SPIE, the International Society for Optical Engineering 2006, vol. 6287, pp. 62870D.1-62870D.

Starzyk JA, et al., "A DC-DC charge pump design based on voltage doublers" IEEE Transaction on Circuits and Systems -I: Fundamental theory and applications, vol. 48, No. 3 Mar. 2001.

Walter P., et al., "Cortical Activation via an implanted wireless retinal prosthesis," Investigative Ophthalmology and Visual Science. 2005;46:1780-1785.

Wu J T. and Chang K L., "MOS charge pumps for low-voltage operation" IEEE Journal of Solid-State Circuits, vol. 33 No. 4 Apr. 1998.

Swain P K., et al., "Back-Illuminated Image Sensors Come to the Forefront. Novel materials and fabrication methods increase quality and lower cost of sensors for machine vision and industrial imaging." Photonics Spectra Aug. 2008.

News Release—Sony develops back-illuminated CMOS image sensor, realizing high picture quality, nearly twofold sensitivity (*1) and low noise, Jun. 2008 http://www.sony.net/SonyInfo/News/Press/200806/08-069E/index.html.

David C Ng, et al., "Pulse frequency modulation based CMOS image sensor for subretinal stimulation" IEEE Transactions on Circuits and Systems-II: Express Briefs, vol. 53, No. 6, Jun. 2006.

An Office Action dated Sep. 28, 2012, which issued during the prosecution of U.S. Appl. No. 13/103,264.

An International Preliminary Report on Patentability dated Jul. 17, 2012, which issued during the prosecution of Applicant's PCT/IL2011/000022.

A Supplementary European Search Report dated Aug. 10, 2012, which issued during the prosecution of Applicant's European Application No. 10 73 8277.

Palanker D. et al., "Design of a high-resolution optoelectric retinal prosthesis". Journal of Neural Engineering, Institute of physics publishing, Bristol, GB. vol. 2, No. 1, Mar. 1, 2005, pp. S105-S120, XP002427333, ISSN: 17412552, DOI: 10.1088/1741-2560/2/1/012.

Cortical Visual Neuro-Prosthesis for the Blind: Retina-Like Software/Hardware Preprocessor, F.J. Pelayol, A. Martinezl, S. Romerol, Ch.A. Morillasl, E. Rosl , E. Fernandez2 1Dept. of Computer Architecture and Technology, University of Granada, Spain 2Dept. of Histology and Institute of Bioengineering, University Miguel Hernandez, Alicante, Spain Neural Engineering, 2003. Conference Proceedings. First International IEEE EMBS Conference.

"Single-Chip CMOS Image Sensors for a Retina Implant System", Markus Schwarz, Ralf Hauschild, Bedrich J. Hosticka, Senior Member, IEEE, Jurgen Huppertz, Student Member, IEEE, Thorsten Kneip, Member, IEEE, Stephan Kolnsberg, Lutz Ewe, and Hoc Khiem Trieu, 2000.

An International Search Report dated Aug. 12, 2011, which issued during the prosecution of Applicant s PCT/IL2011/000022.

An International Search Report and a Written Opinion both dated Sep. 17, 2012, which issued during the prosecution of Applicant's PCT/IL12/00057.

An Official Action dated Dec. 7, 2012, issued during prosecution of U.S. Appl. No. 12/678,509.

An Official Action dated Dec. 14, 2012, which issued during the prosecution of U.S. Appl. No. 13/034,516.

International Search Report dated Sep. 4, 2012, during prosecution of PCT/IL2012/000186.

Humayun, et al, "Visual Pereception in a Blind Subject with a Chronic Microelectric Retinal Prosthesis", Vision Research 43 (2003), pp. 2573-2581.

Walter, et al., "Cortical Activation via an Implanted Wireless Retinal Prosthesis", Investigative Ophthalmology & Visual Science, vol. 46. No. 5 (May 2005) pp. 1780-1785.

Ganesan et al, "Diamond Penetrating Electrode Array for Epi-Retinal Prothesis", 3rd Annual International Conference of IEEE EMBS, Buenos Aires, Argentina (Aug. 31-Sep. 4, 2010), pp. 6757-6760.

Schwarz et al, "Hardware Architecture of Neural Net Based Retina Implant for Patients Suffering from Retinitis Pigementosa", Fraunhofer Institute of Microelectric Circuits and Systems Finkenstr. 61, IEEE (1996), pp. 653-658.

* cited by examiner

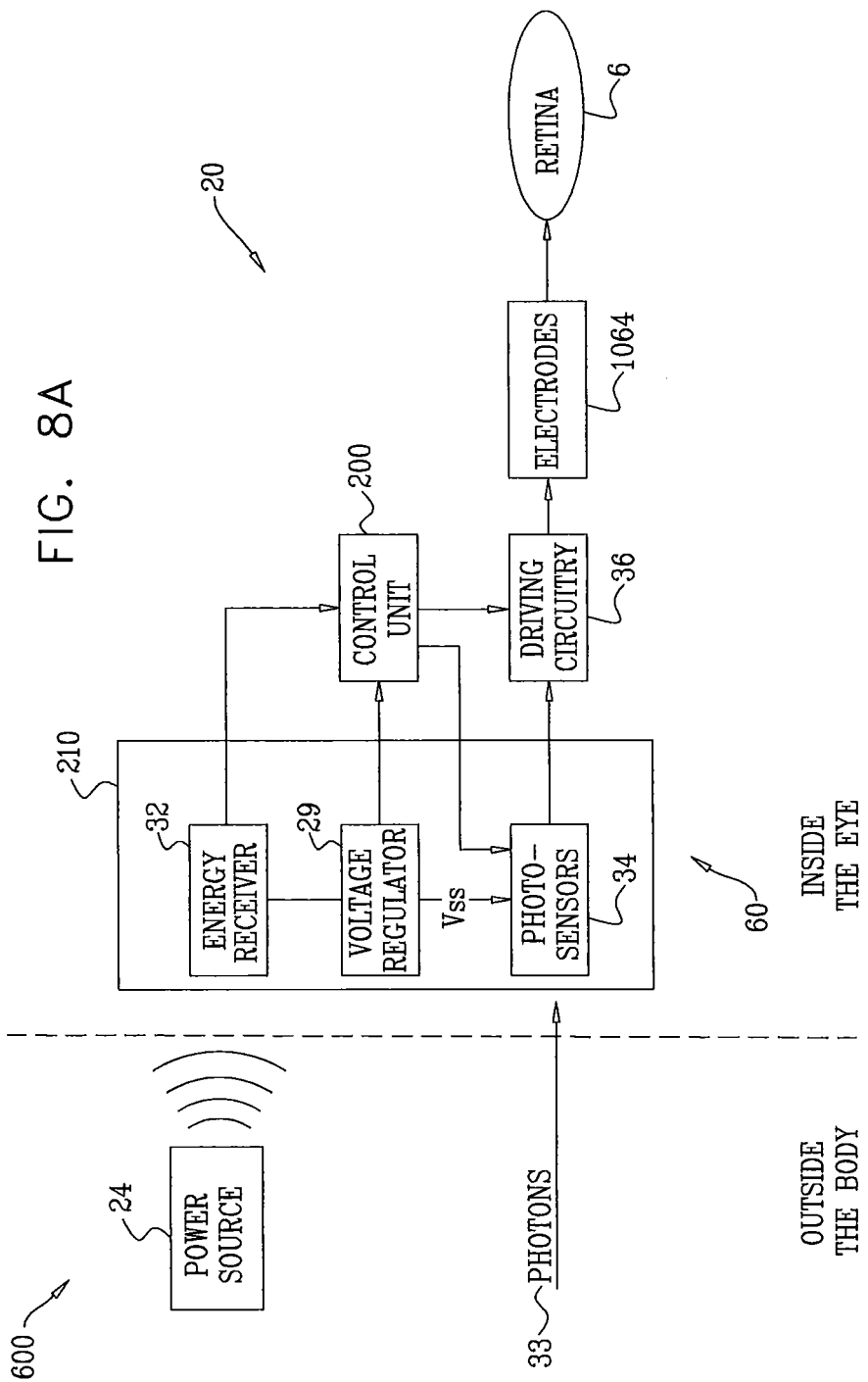

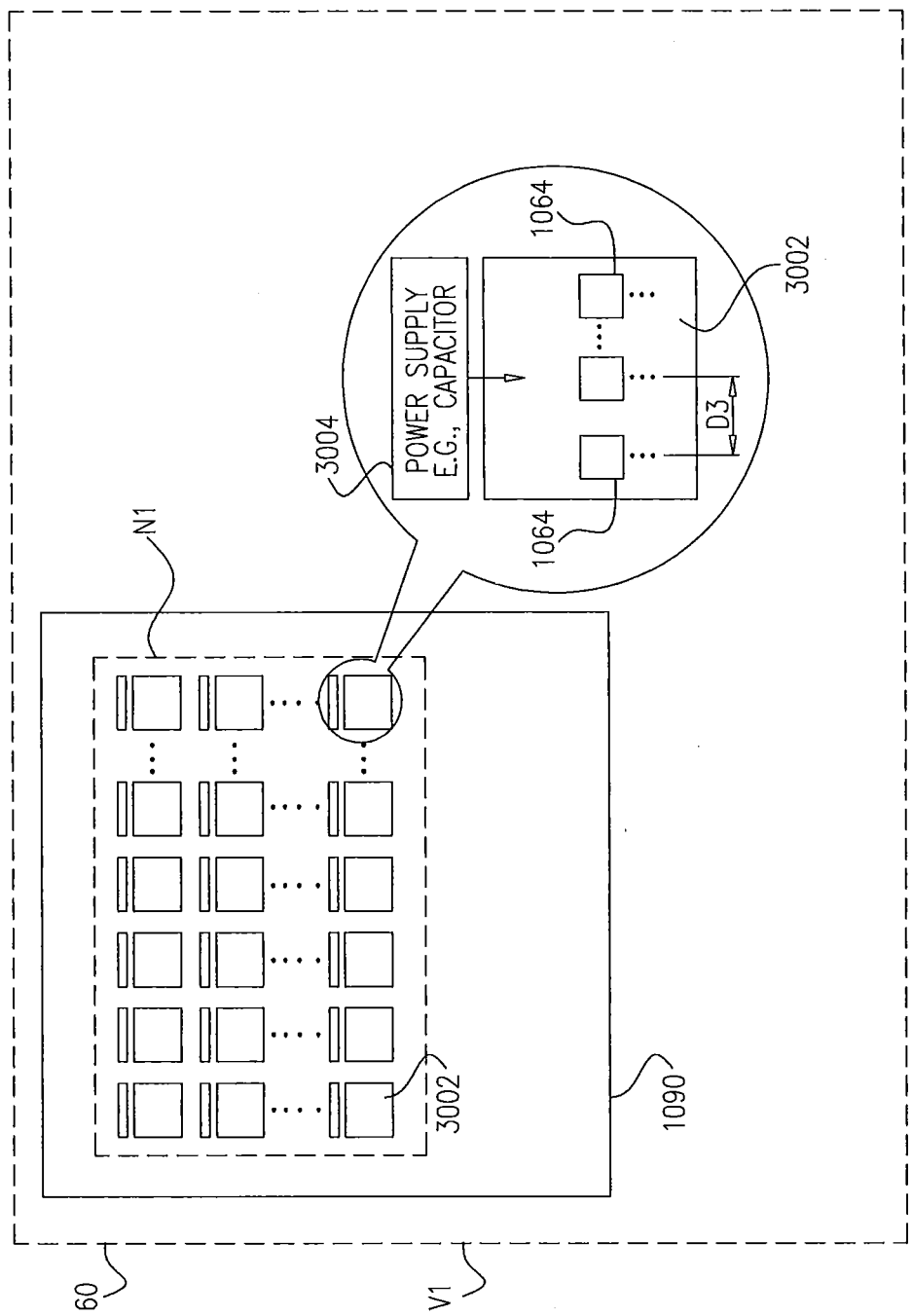

RETINAL PROSTHESIS TECHNIQUES

FIELD OF EMBODIMENTS OF THE INVENTION

Some applications of the invention relate generally to implantable medical devices and more specifically to a retinal prosthesis.

BACKGROUND

Retinal malfunction, due to degenerative retinal diseases, is a leading cause of blindness and visual impairment. Implantation of a retinal prosthesis is a technology for restoring some useful vision in individuals suffering from retinal-related blindness.

The retina is a multi-layered light-sensitive structure that lines the posterior, inner part of the eye. The retina contains photoreceptor cells, for example rods and cones, which capture light and convert light signals into neural signals transmitted through the optic nerve to the brain. Rods are responsible for light sensitive, low resolution black and white vision, whereas cones are responsible for high resolution color vision. Most cones lie in the fovea, which defines the center of the retina. A bipolar cell layer exists between the photoreceptors and ganglion cells of the retina. The bipolar cell layer transmits signals from the photoreceptors to the ganglion cells whose axons form the optic nerve and transmit visual information to the brain.

Grill W., et al. describe in an article, entitled "Implanted Neural Interfaces: Biochallenges and Engineered Solutions," Annu. Rev. Biomed. Eng. 2009. 11:1-24, a regenerative sieve electrode that has holes to allow processes from a severed neuron to grow through. The article includes a schematic illustration of a sieve electrode.

U.S. Pat. No. 6,908,470 to Stieglitz describes a sieve electrode for connection to a nerve stump, which is composed of a thin flexible substrate with a plurality of ports for nerve filaments and several electrodes that are disposed on at least some of said ports on said substrate and adapted for being electrically contacted via conductors on said substrate, as well as of at least one counter-electrode. The substrate presents tabs protruding from the edge for fixing the substrate on a face of the nerve stump, which serve, at the same time, as carrier of the counter electrode. With this sieve electrode a neuro-technological interface is provided that is described as permitting a low-lesion contact with the nerve stump at a maximum of useable surface for the ports.

U.S. Pat. No. 4,969,468 to Byers describes an electrode array device for making multiple electrical contacts with cellular tissue or organs. The electrode array includes a base, a two dimensional array of conducting protuberances arising from the base and serving as electrodes, and conductors embedded onto the base and connected to such protuberances for transmitting electrical signals to and/or from the protuberances. The protuberances may also include an insulating layer which covers either the entire protuberance or which leaves the tips exposed for making focused electrical contact. Electrode arrays may be used singly or in combination with a second electrode array so as to form a sandwich around a target tissue. The sandwich electrode array may employ indexing cones for aligning the opposing electrode arrays and for limiting their vertical proximity. The conductors of the electrode array may be electronically connected or coupled to processing circuitry which amplifies and analyzes the signal received from the tissue and/or which generates signals which are sent to the target tissue and possibly coordinates the generated signals with signals which originate with the tissue.

The following patents and patent application publications may be of interest:

U.S. Pat. No. 1,662,446
U.S. Pat. No. 2,721,316
U.S. Pat. No. 2,760,483
U.S. Pat. No. 4,272,910
U.S. Pat. No. 4,551,149
U.S. Pat. No. 4,601,545
U.S. Pat. No. 4,628,933
U.S. Pat. No. 4,664,117
U.S. Pat. No. 4,837,049
U.S. Pat. No. 4,903,702
U.S. Pat. No. 5,016,633
U.S. Pat. No. 5,024,223
U.S. Pat. No. 5,108,427
U.S. Pat. No. 5,109,844
U.S. Pat. No. 5,133,356
U.S. Pat. No. 5,147,284
U.S. Pat. No. 5,159,927
U.S. Pat. No. 5,397,350
U.S. Pat. No. 5,411,540
U.S. Pat. No. 5,476,494
U.S. Pat. No. 5,526,423
U.S. Pat. No. 5,575,813
U.S. Pat. No. 5,674,263
U.S. Pat. No. 5,575,813
U.S. Pat. No. 5,597,381
U.S. Pat. No. 5,800,533
U.S. Pat. No. 5,800,535
U.S. Pat. No. 5,836,996
U.S. Pat. No. 5,837,995
U.S. Pat. No. 5,865,839
U.S. Pat. No. 5,873,901
U.S. Pat. No. 5,895,415
U.S. Pat. No. 5,935,155
U.S. Pat. No. 5,944,747
U.S. Pat. No. 6,032,062
U.S. Pat. No. 6,230,057
U.S. Pat. No. 6,298,270
U.S. Pat. No. 6,324,429
U.S. Pat. No. 6,368,349
U.S. Pat. No. 6,389,317
U.S. Pat. No. 6,442,431
U.S. Pat. No. 6,473,365
U.S. Pat. No. 6,507,758
U.S. Pat. No. 6,611,716
U.S. Pat. No. 6,658,299
U.S. Pat. No. 6,677,225
U.S. Pat. No. 6,678,458
U.S. Pat. No. 6,755,530
U.S. Pat. No. 6,762,116
U.S. Pat. No. 6,770,521
U.S. Pat. No. 6,923,669
U.S. Pat. No. 6,976,998
U.S. Pat. No. 7,003,354
U.S. Pat. No. 7,006,873
U.S. Pat. No. 7,025,619
U.S. Pat. No. 7,027,874
U.S. Pat. No. 7,031,776
U.S. Pat. No. 7,037,943
U.S. Pat. No. 7,047,080
U.S. Pat. No. 7,081,630
U.S. Pat. No. 7,096,568
U.S. Pat. No. 7,103,416
U.S. Pat. No. 7,107,097

U.S. Pat. No. 7,139,612
U.S. Pat. No. 7,162,308
U.S. Pat. No. 7,251,528
U.S. Pat. No. 7,321,796
US Patent Application Publication 2006/0282128
US Patent Application Publication 2007/0191909
US Patent Application Publication 2010/0174224
PCT WO 2003/32946
PCT WO 2001/91854
PCT WO 2007/09539

The following articles may be of interest:

David C N G, et al., "Pulse frequency modulation based CMOS image sensor for subretinal stimulation" IEEE Transactions on Circuits and Systems-II: Express Briefs, Volume 53, No 6, June 2006.

Jourdain R P., et al., "Fabrication of piezoelectric thick-film bimorph micro-actuators from bulk ceramics using batch-scale methods" Multi-Material Micro Manufacture, S. Dimov and W. Menz (Eds.) 2008 Cardiff University, Cardiff, UK., Whittles Publishing Ltd.

Kim B., "Through-Silicon-Via Copper Deposition for Vertical Chip Integration" Master. Res. Soc. Symp. Proc. Vol. 970, 2007 Material Research Society Lianga C, et al., "Surface modification of cp-Ti using femtosecond laser micromachining and the deposition of Ca/P layer" Materials Letters Volume 62, Issue 23, 31 Aug. 2008, Pages 3783-3786.

Puech M., et al., "Fabrication of 3D packaging TSV using DRIE" ALCATEL Micro Machining Systems, www.adixen-.com Seo J M., et al., "Biocompatibility of polyimide microelectrode array for retinal stimulation," Materials Science and Engineering: C, Volume 24, Number 1, 5 Jan. 2004, pp. 185-189(5)"

Sorkin R., et al., "Process entanglement as a neuronal anchorage mechanism to rough surfaces," Nanotechnology 20 (2009) 015101 (8pp)

Starzyk J A, et al., "A DC-DC charge pump design based on voltage doublers" IEEE Transaction on Circuits and Systems-I: Fundamental theory and applications, Volume 48, No 3 March 2001.

Stein D J, et al., "High voltage with Si series photovoltaics" Proceedings of SPIE, the International Society for Optical Engineering 2006, vol. 6287, pp. 62870D.1-62870D.

Swain P K., et al., "Back-Illuminated Image Sensors Come to the Forefront. Novel materials and fabrication methods increase quality and lower cost of sensors for machine vision and industrial imaging." Photonics Spectra August 2008.

Vorobyeva A Y. et al., "Metallic light absorbers produced by femtosecond laser pulses," Advances in Mechanical Engineering, Volume 2010, Article ID 452749, 4 pages doi: 10.1155/2010/452749

Vorobyeva A Y. et al., "Femtosecond laser structuring of titanium implants," Applied Surface Science, Volume 253, Issue 17, 30 Jun. 2007, Pages 7272-7280.

Wallman L., et al., "The geometric design of micromachined silicon sieve electrodes influences functional nerve regeneration," Biomaterials 2001 May:22(10):1187-93

Walter P., et al., "Cortical Activation via an implanted wireless retinal prosthesis," Investigative Ophthalmology and Visual Science. 2005; 46:1780-1785

Wu J T. and Chang K L., "MOS charge pumps for low-voltage operation" IEEE Journal of Solid-State Circuits, Volume 33 No. 4 April 1998.

Zrenner E., 2002, "Will retinal implants restore vision?" Science 295(5557), pp. 1022-5.

http://www.sony.net/SonyInfo/News/Press/200806/08-069E/index.html

SUMMARY OF APPLICATIONS OF THE INVENTION

In some applications of the present invention, a system is provided for restoring at least partial vision in a subject suffering from a retinal disease. The system comprises an apparatus comprising an external device, comprising a mount that is placed in front of the subject's eye. The mount may be, for example, a pair of eyeglasses. The external device further comprises a power source, for example a laser that is coupled to the mount and is configured to emit radiated energy that is outside the visible range directed toward the subject's eye.

The apparatus additionally comprises an intraocular device, which is implanted entirely in the subject's eye. The intraocular device comprises an intraocular retinal prosthesis, configured to be implanted in the subject's eye in either an epi-retinal or a sub-retinal position.

The intraocular device typically comprises a support substrate and an array of electrodes protruding from the support substrate. (In this context, in the specification and in the claims, "array" is meant to include rectangular as well as non-rectangular arrays (such as circular arrays). The protruding electrodes are shaped to define electrically-exposed tips which penetrate retinal tissue of the subject, bringing the electrodes in contact with the tissue. For some applications, a surface of the electrodes is treated to increase roughness and surface area of the electrodes, thus reducing electrode impendence and facilitating retinal stimulation and/or axon regeneration. Additionally or alternatively, the exposed tips of the electrodes have perforations passing therethrough, further increasing the surface area of the electrodes and allowing neuronal processes, to pass through and intertwine with the electrodes.

For some applications, the support substrate from which the electrodes protrude comprises additional elements of a retinal prosthesis, e.g., an energy receiving layer, a photosensor layer and driving circuitry that is powered by the energy receiving layer. The driving circuitry typically drives electrical charge into the retinal tissue from the tips of the electrodes, in response to sensing by the photosensor layer, in order to stimulate the retinal tissue.

For some applications, the photosensor layer is divided into units, each unit corresponding to a stimulating electrode in the array of electrodes.

The inventors have identified that, for some applications, sufficient stimulation of retinal tissue is a characteristic for consideration in enabling proper function of a retinal prosthesis. In particular, facilitating stimulation of the bipolar cell layer of the retina, which in turn stimulates ganglion cells, is a characteristic for consideration in retinal prosthesis provided by some applications of the present invention. The ganglion cells, whose axons form the optic nerve, further transmit the visual information to the brain resulting in the formation of an image. Penetrating perforated electrodes, in contrast to surface electrodes known in the art which sit on the surface of tissue, are configured to extend from either an epi-retinal or a sub-retinal implantation site and penetrate retinal tissue to directly contact and drive electrical charge into the bipolar cell layer from typically less than 10 um from the nearest bipolar cell. Rough electrode surfaces and perforations passing through the electrodes allow neuronal processes to grow therethrough, further improving cell-electrode coupling and increasing stimulation. Increased and direct contact of the retinal tissue by penetrating perforated electrodes enhances stimulation of the retina resulting in enhanced image resolution.

There is therefore provided in accordance with an application of the present invention, apparatus including:
- an external device, including:
  - a mount, configured to be placed in front of an eye of a subject; and
  - a power source coupled to the mount and configured to emit energy toward the eye; and
- an intraocular device configured to be implanted entirely in the subject's eye, the intraocular device including:
  - an energy receiver, configured to receive the energy from the power source and to generate a voltage drop in response thereto;
  - a control unit;
  - a plurality of stimulating electrodes;
  - a plurality of photosensors, each photosensor configured to detect photons and to generate a signal in response thereto; and
  - driving circuitry, coupled to the energy receiver and to the photosensors, and configured to utilize the voltage drop to drive the electrodes to apply electrical charges to a retina of the eye in response to the signals from the photosensors, the external device is configured to modulate the energy emitted from the power source, and the control unit is configured to demodulate the modulated energy and in response regulate an operation parameter of the intraocular device.

For some applications, the apparatus includes a control element configured to receive an input from the subject, the external device is configured to modulate the energy emitted from the power source in response to the input.

For some applications, the operation parameter includes a characteristic of the electrical charges applied by the electrodes, and the control unit is configured to regulate the characteristic of the electrical charges applied by the electrodes.

For some applications, the characteristic of the electrical charges is a temporal characteristic of the electrical charges.

For some applications, the driving circuitry is configured to drive the electrodes to apply the electrical charges in pulses of electrical charge, and the temporal characteristic of the electrical charges is selected from the group consisting of: a number of the pulses, a frequency of the pulses, a duration of each pulse, and a pulse repetition interval of the pulses.

For some applications, the operation parameters include a sensitivity of the photosensors, and the control unit is configured to control the sensitivity of the photosensors.

For some applications, the sensitivity of the photosensors includes a duration of a sensing period of the photosensors, and the control unit is configured to regulate the duration of the sensing period of the photosensors.

For some applications, the operation parameters include a duration of an energy receiving period of the energy receiver, and the control unit is configured to regulate the duration of the energy receiving period of the energy receiver.

There is further provided, in accordance with an application of the present invention, apparatus including:
- an external device, including:
  - a mount, configured to be placed in front of an eye of a subject; and
  - a power source coupled to the mount and configured to emit energy toward the eye; and
- an intraocular device configured to be implanted entirely in the subject's eye, the intraocular device including:
  - an energy receiver, configured to receive the energy from the power source and to generate a voltage drop in response thereto;
  - a plurality of stimulating electrodes;
  - a plurality of photosensors, each photosensor configured to detect photons and to generate a signal in response thereto;
  - a control unit configured to regulate operation parameters of the intraocular device, in response to the signals from the photosensors; and
  - driving circuitry, coupled to the energy receiver and to the photosensors, and configured to utilize the voltage drop to drive the electrodes to apply electrical charges to a retina of the eye in response to the signals from the photosensors.

For some applications, the control unit is configured to regulate operation parameters of the intraocular device by applying a logarithmic transformation to the signal received by the photosensors.

For some applications, the operation parameters include a characteristic of the electrical charges applied by the electrodes, and the control unit is configured to regulate the characteristic of the electrical charges applied by the electrodes.

For some applications, the characteristic of the electrical charges is a temporal characteristic of the electrical charges.

For some applications, the driving circuitry is configured to drive the electrodes to apply the electrical charges in pulses of electrical charge, and the temporal characteristic of the electrical charges is selected from the group consisting of: a number of the pulses, a frequency of the pulses, a duration of each pulse, and a pulse repetition interval of the pulses.

For some applications, the operation parameters include a sensitivity of the photosensors, and the control unit is configured to control the sensitivity of the photosensors.

For some applications, the sensitivity of the photosensors includes a duration of a sensing period of the photosensors, and the control unit is configured to regulate the duration of the sensing period of the photosensors.

For some applications, the operation parameters include a duration of an energy receiving period of the energy receiver, and the control unit is configured to regulate the duration of the energy receiving period of the energy receiver.

For some applications, the control unit is configured to perform image processing in response to the signal generated by the plurality of photosensors.

For some applications, the control unit is configured to perform the image processing utilizing a process selected from a group consisting of: edge detection, focusing, light adjustment, averaging, and motion detection.

For some applications, the plurality of photosensors are color sensitive, and the driving circuitry is configured to regulate electrical charges driven through the electrodes in response to a color sensed by the photosensors.

For some applications, the driving circuitry is configured to create distinct stimulation patterns of the electrical charges applied to the retina, in response to the color sensed by the photosensors.

For some applications, the driving circuitry is configured to drive a first one of the electrodes to apply an electrical charge in response to the sensed color being a first color, and the driving circuitry is configured to drive a second one of the electrodes to apply an electrical charge in response to the sensed color being a second color.

There is still further provided, in accordance with an application of the present invention, apparatus configured for implantation in a body of a subject, the apparatus including:

an implantable array of at least 10 subsets of 3 or more electrodes; and for each subset, a respective common power supply configured to provide current to the electrodes in the subset, at least some of the electrodes in each subset are configured to drive respective electrical charges into tissue of the subject.

For some applications, the common power supply for each subset includes a common capacitor for each subset.

For some applications, the at least 10 subsets include 10-2500 subsets.

For some applications, a total volume of the apparatus is less than 0.2 cc.

For some applications, an electrode in at least one of the subsets is within 500 um of another electrode in the subset.

For some applications, an electrode in at least one of the subsets is within 300 um of another electrode in the subset.

There is additionally provided, in accordance with an application of the present invention, apparatus including:
an external device, including:
 a mount, configured to be placed in front of an eye of a subject; and
 a power source coupled to the mount and configured to emit energy toward the eye; and
an intraocular device configured to be implanted entirely in the subject's eye, the intraocular device including:
 a light receiving element configured to switch between:
  a first time period, during which the light receiving element receives the energy from the power source and generates a voltage drop in response thereto; and
  a second time period, during which the light receiving element detects photons and generates a signal in response thereto;
 a control unit configured to regulate the switch between the first and second time periods;
 a plurality of stimulating electrodes; and
 driving circuitry, coupled to the light receiving element, and configured to utilize the voltage drop to drive the electrodes to apply electrical charges to a retina of the eye in response to the signal from the light receiving element.

There is yet additionally provided, in accordance with an application of the present invention, apparatus including:
an external device, including:
 a mount, configured to be placed in front of an eye of a subject; and
 a power source coupled to the mount and configured to emit energy toward the eye; and
an intraocular device configured to be implanted entirely in the subject's eye, the intraocular device including:
 an energy receiver, configured to receive the energy from the power source and to generate a voltage drop in response thereto;
 a plurality of stimulating electrodes;
 a plurality of uncooled infrared detectors configured to detect incident infrared radiation and generate a signal in response thereto;
 driving circuitry, coupled to the energy receiver and to the uncooled infrared detectors, and configured to utilize the voltage drop to drive the electrodes to apply electrical charges to a retina of the eye in response to the signals from the infrared detectors.

There is yet additionally provided, in accordance with an application of the present invention, apparatus configured for implantation in an eye of a subject, the apparatus including:
an intraocular device including:
 a plurality of photosensors, each photosensor configured to detect photons and to generate a signal in response thereto;
 an array of at least 10 subsets of two or more electrodes; and
 a control unit, configured to drive at least some of the electrodes in each subset to non-simultaneously apply respective electrical charges into a retina of the subject, in response to photons detected generally simultaneously by respective ones of the photosensors.

For some applications, the control unit is configured such that the electrical charge driven by each electrode in a subset is returned via a plurality of the other electrodes in the subset.

For some applications, the control unit is configured such that the electrical charge driven by each electrode in a subset is returned via all of the other electrodes in the subset.

For some applications, the control unit is configured such that the electrical charge driven by each electrode in a subset is returned via an electrode in the subset that serves as a common return electrode for the other electrodes in the subset.

There is still additionally provided, in accordance with an application of the present invention, apparatus including:
an external device, including:
 a mount, configured to be placed in front of an eye of a subject; and
 a power source coupled to the mount and configured to emit energy toward the eye; and
an intraocular device configured to be implanted entirely in the subject's eye, the intraocular device including a die including:
 an energy receiver, configured to receive the energy from the power source and to generate a voltage drop in response thereto; and
 a plurality of photosensors, each photosensor configured to detect photons and to generate a signal in response thereto.

For some applications, the die includes:
a plurality of stimulating electrodes; and
driving circuitry, coupled to the energy receiver and to the photosensors, and configured to utilize the voltage drop to drive the electrodes to apply electrical charges to a retina of the eye in response to the signals from the photosensors.

For some applications, the die further includes a charge pump configured to generate a voltage to be supplied to at least one component of the intraocular device.

For some applications, the external device is configured to modulate the energy emitted from the power source, and the die includes a control unit configured to demodulate the modulated energy and, in response, regulate an operation parameter of the intraocular device.

For some applications, the external device is configured to modulate the energy emitted from the power source, and the die includes a demodulator configured to demodulate the modulated energy and, in response, regulate an operation parameter of the intraocular device.

For some applications, the apparatus includes an additional die, the additional die including:
a plurality of stimulating electrodes; and
driving circuitry, coupled to the energy receiver and to the photosensors, and configured to utilize the voltage drop to drive the electrodes to apply electrical charges to a retina of the eye in response to the signals from the photosensors.

For some applications, the additional die includes a charge pump configured to generate a voltage to be supplied to the intraocular device.

For some applications, the external device is configured to modulate the energy emitted from the power source, and wherein the additional die includes a control unit configured to demodulate the modulated energy and, in response, regulate an operation parameter of the intraocular device.

For some applications, the external device is configured to modulate the energy emitted from the power source, and wherein the additional die includes a demodulator configured to demodulate the modulated energy and, in response, regulate an operation parameter of the intraocular device.

BRIEF DESCRIPTION OF THE DRAWINGS

FIGS. 8A-B (herein, "FIG. 8") are a block diagram (FIG. 8A), and a schematic illustration (FIG. 8B) of the transmission of energy, information, and instructions, in the system for restoring vision, in accordance with some applications of the present invention;

DETAILED DESCRIPTION OF EMBODIMENTS

Figure 1:
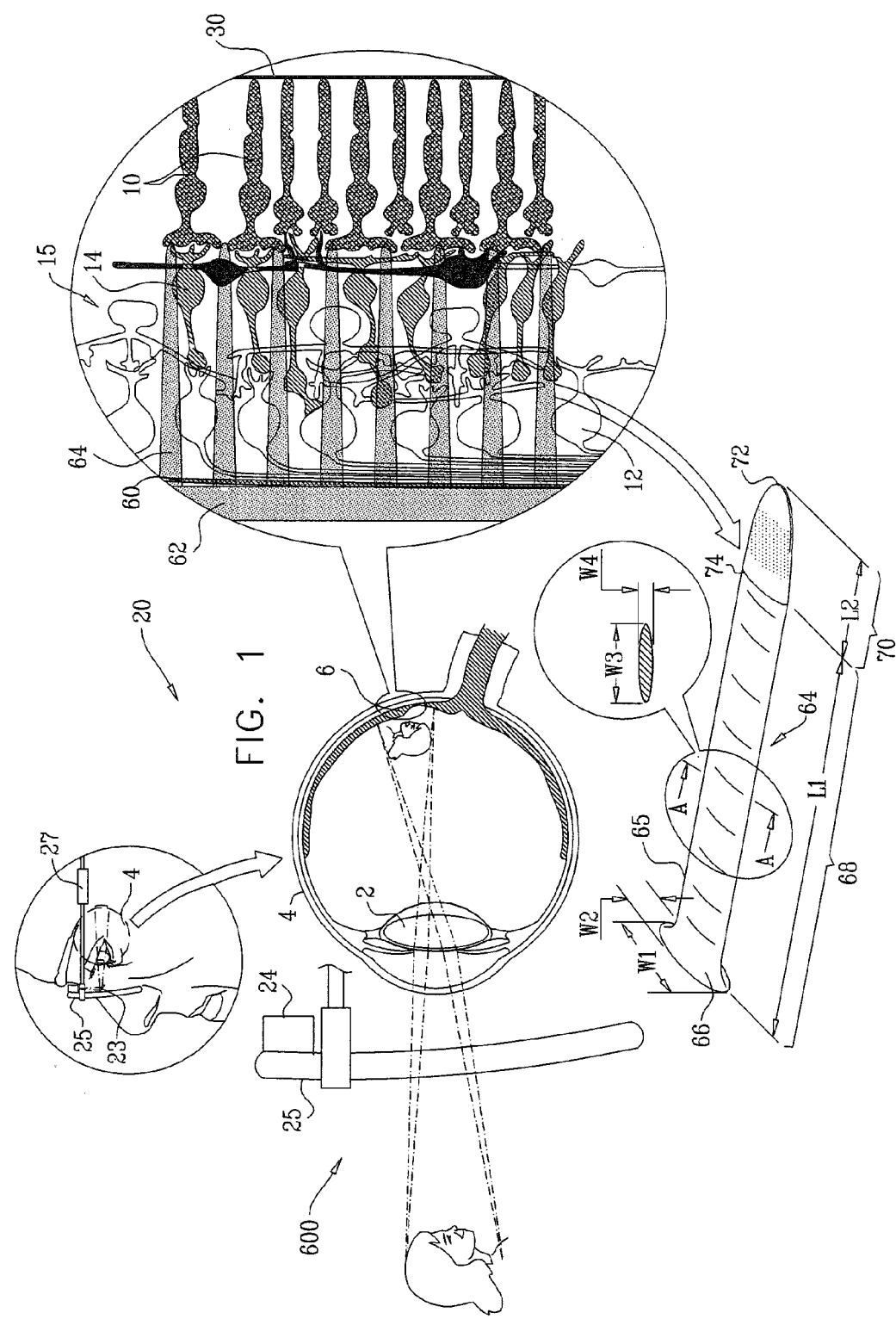
FIG. 1 shows a system for restoring at least partial vision in a subject in accordance with some applications of the present invention.

FIG. 1 shows a system 20 for restoring at least partial vision in a subject, a portion of which is implanted in an eye of the subject, in accordance with some applications of the present invention.

Vision is initiated when light reflecting from objects is focused by lens 2 of eye 4 onto the retina 6. FIG. 1 shows a cross section of a portion of a human retina. The retina is approximately 0.2-0.5 mm thick and lines the back of the eye. As shown, the retina consists of three layers of neurons: photoreceptor cells 10, ganglion cells 12 and many interneurons 15 packed into the central part of the section of the retina intervening between the photoreceptors and the ganglion cells. The ganglion cells, which transmit visual information to the brain, lie innermost (as used herein) in the retina, i.e., on the side of the retina closest to the lens and front of the eye. The photoreceptor cells (e.g., rods and cones), which capture light and convert light signals into neural signals, lie outermost in the retina. The central part of the section of retina located between the photoreceptors and the ganglion cells includes the inner nuclear layer (INL), which is made up of bipolar cells 14 and other cells. Interneurons 15, e.g., horizontal cells and amacrine cells, facilitate regulation of the neural signal from the photoreceptors and the bipolar cells.

Bipolar cells 14 typically transmit signals from photoreceptors 10 to ganglion cells 12. The rod and cone photoreceptors transfer a signal to the bipolar cells that lay adjacent to the photoreceptor layer. The bipolar cells then transmit the signal to the ganglion cells whose axons form the optic nerve. The bipolar cell 14 are generally located in a region of the retina that is approximately 130 um-200 um from the inner limiting membrane (ILM), which is the boundary between the vitreous humor in the posterior chamber and the retina itself.

As shown in FIG. 1, for some applications, an intraocular device 60 is implanted in an epi-retinal position, typically coupled to the ILM. As described in Zrenner, 2002, which is incorporated herein by reference, epi-retinal arrays are typically implanted onto the retinal surface that separates the retinal neural layer from the vitreous body of the eye's posterior chamber, such that the implant is typically located outside of the vitreous body, contacting the ILM. As appropriate, techniques described in one or more of these references may be adapted for use in implanting device 60.

For some applications, device 60 is implanted in a subretinal position (not shown). As described in Zrenner, 2002, which is incorporated herein by reference, sub-retinal arrays are typically implanted between the pigment epithelial layer 30 and the layer of the retina which contains photoreceptor cells 10.

As provided by some applications of the present invention, device 60 comprises a support substrate 62 and a plurality of electrodes 64 protruding from the support substrate. Support substrate 62 comprises components of an intraocular retinal prosthesis. For example, support substrate 62 may comprise an energy receiving layer, a photosensor layer and driving circuitry. The driving circuitry is powered by the energy receiving layer, which typically receives energy from an external device 600 comprising an external power source 24 (e.g., a laser coupled to the frame of a pair of eyeglasses 25, and/or a radiofrequency (RF) power source, and/or another electromagnetic power source). For some applications a partially-transparent (e.g., half-silvered) mirror 23 is coupled to eyeglasses 25, providing ophthalmoscope functionality to the external device.

It is to be noted that for some applications, techniques and apparatus described herein with reference to the external and intraocular devices may be performed with techniques and apparatus described in U.S. patent application Ser. No. 12/368,150 to Gross, et al., entitled, "Retinal Prosthesis," filed Feb. 9, 2009, which issued as U.S. Pat. No. 8,150,526 to Gross et al., U.S. patent application Ser. No. 12/687,509 to Gefen et al., entitled "Penetrating electrodes for retinal stimulation, filed Jan. 14, 2010, which published as US 2011/0172736 to Gefen et al., and/or PCT/IL2010/000097 to Gross et al., entitled "Retinal Prosthesis," filed Feb. 3, 2010, which published as WO/2010/089739 to Gross et al., all of which are assigned to the assignee of the present patent application and are incorporated herein by reference.

The driving circuitry drives electrodes 64 to apply electrical charges to the retina, in response to sensing by the photosensor layer, in order to stimulate the retina 6. Accordingly, system 20 for restoring vision in a subject does not comprise an extraocular camera, and intraocular device 60 does not receive image data from outside the eye, but rather utilizes the intact optics and processing mechanisms of the eye 4.

Intraocular device 60 typically comprises approximately 500-6000, e.g., 1000-4000, typically 1600 electrodes 64. For some applications, the electrodes protrude perpendicularly at least 50 um from the support substrate.

Each electrode is typically 100-1000 um in length e.g., 300-600 um, for example, 400 um, in order to reach the outer plexiform layer (OPL), where connections between the bipolar cells and the adjacent photoreceptor cells occur. For some applications, each electrode comprises an electrically-insulated body portion 68 coupled to an electrically exposed tip portion 70. Insulated portion 68 of the electrode has a length L1 of between 100 um and 650 um, e.g., 150 um. Exposed tip 70 of electrode 64 typically has a length L2 of between 25 um and 100 um, e.g., 50 um. Typically, electrode 64 has an exposed area of 750 um2. The electrodes 64 protrude from support substrate 62, such that when device 60 is implanted in an eye of a subject, electrodes 64 penetrate tissue of retina 6 and exposed tip portions 70 are typically disposed in layer of bipolar cells 14. Other dimensions of the electrodes are described hereinbelow, with reference to FIGS. 2-3.

FIG. 1 shows a schematic illustration of electrode 64, in accordance with some applications of the present invention. As shown, the insulated portion 68 of electrode 64 includes an elliptical proximal base portion 66 and an elongated body portion 65 extending between the base portion and the exposed tip 70. Tip 70 typically comprises distal tip 72 and tip base 74. Base portion 66 typically has a major axis W1 of between 25 um and 200 um, e.g., 100 um, and a minor axis W2 that is typically 10-100 um, e.g., 50 um. Base portion 66 typically has a larger average diameter than body portion 65, contributing to the structural strength of electrode 64. Body portion 65 is typically generally elliptical, and has a major axis W3 of between 15 um and 60 um, e.g., 30 um, and a minor axis W4 between 5 um and 20 um, e.g., 10 um. Typically, electrodes 64 have a cross-section of 50-200 um2, 20 um from distal tip 72. For some applications electrodes 64 have a cross-section of at least 200 um2, 20 um from distal tip 72.

For some applications, each electrode 64 is typically 25-100 um in length e.g., 50 um, in order to penetrate the nerve fiber layer (NFL) and reach the layer of ganglion cells 12 (GCL). Contacting the ganglion cells by electrodes 64 typically enables the use of a reduced amount of power in order to stimulate the ganglion cells. Close proximity to ganglion cells 12 generally results in more focused stimulation that enables higher pixel density for a given amount of electrical charge.

Figure 2A:
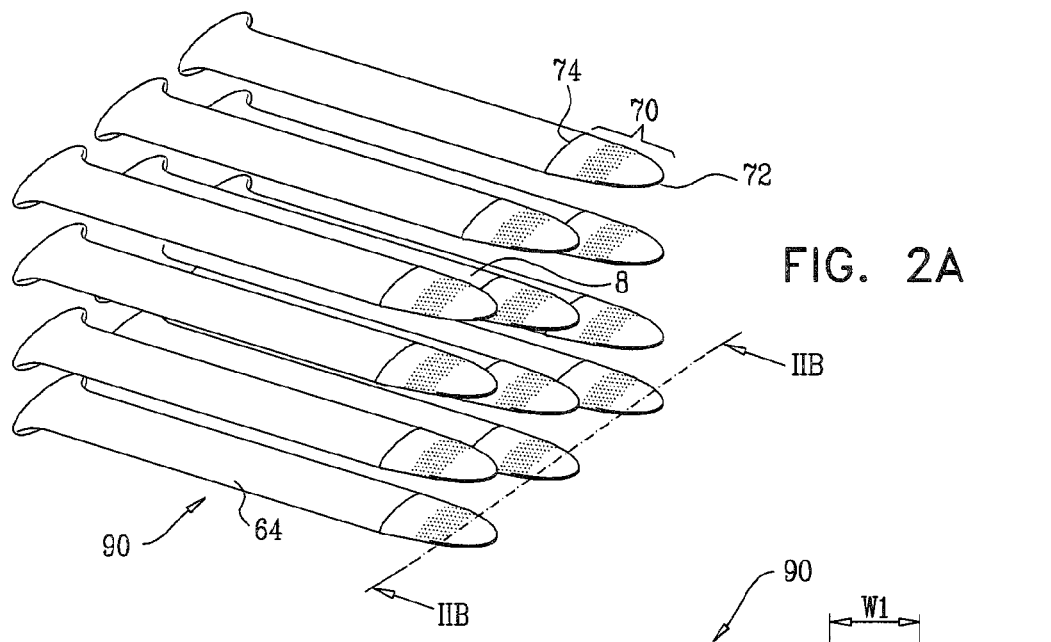
FIGS. 2A-B are schematic illustrations of an array of penetrating electrodes, in accordance with some applications of the present invention.

Reference is made to FIG. 2A, which is a schematic illustration of an array 90 of electrode 64, in accordance with some applications of the present invention. Tip portions 70 of electrodes 64 are typically shaped to define a plurality of perforations passing therethrough. In some applications, tips 70 are generally pointed, to facilitate tissue penetration. The perforated configuration of the tip allows for neuronal processes to intertwine with the electrode tips when electrodes 64 are disposed in retinal tissue of a subject. Increased and direct contact between the electrodes and the neuronal processes, improves the interaction between the neurons, e.g., bipolar cells, and the electrodes. Improved neuron/electrode interaction and coupling enhances stimulation of the neurons by the electrodes. Each tip 70 is typically shaped to define between 1 and 50 perforations (e.g., 1-10) passing therethrough. For some applications, the perforations of each electrode are located 5-20 um (e.g., 10 um) from distal tip 72 and 10-30 um from tip-base 74.

Typically, a spatial density of the perforations of each pointed tip is 0.001-0.02 perforations/um2, or 0.02 to 0.5 perforations/um2, e.g., 0.1 perforations/um2. For some applications, each perforation has a diameter of 1-10 um. The diameter of the perforations in electrode 64 allows axons of bipolar cells, which typically have an average diameter of 1 um, to penetrate and grow through the perforations.

As mentioned hereinabove, for some applications electrodes 64 are disposed in the layer of ganglion cells 12. In such applications, the axons of the ganglion cells grow through the perforations in electrode tips 70, increasing coupling between the neuronal processes and electrodes 64, and improving stimulation of the ganglion cell layer.

The average diameter of the perforations is typically smaller than the average diameter of a retinal glial cell, which is typically larger than 10 um, preventing glial cells from passing through the perforations in the electrode. Preventing glial cells from passing through the perforations reduces glial encapsulation of the electrodes, and prolongs electrode function.

The perforations are typically created by use of chemical treatments e.g., etching and/or a laser beam. For some applications, the same treatment is used to create the perforations and to increase surface roughness. For some applications, a surface of tip 70 of electrode 64 is coated with carbon nanotubes, attracting neuronal processes to the perforations in tip 70 and increasing adhesion of the neuronal processes to the perforations. Typically, the carbon nanotube coating within the perforation can withstand penetration of neuronal processes into the perforations.

Figure 2B:
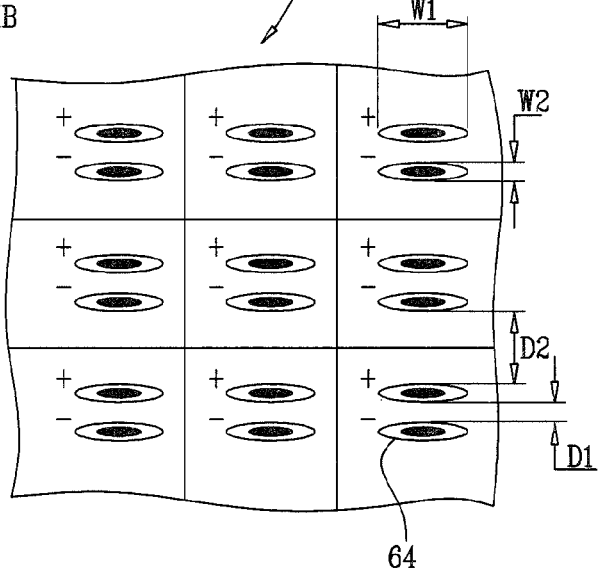

Reference is made to FIG. 2B, which is a schematic illustration of an end view of array 90 of electrodes 64, in accordance with some applications of the present invention. Device 60 typically comprises array 90 of electrodes 64 comprising at least 40 electrodes per mm2, e.g., between 100 and 400 electrodes per mm2. FIG. 2B shows array 90 divided into nine units by way of illustration and not limitation. For some applications, each unit is 100 um×100 um in size. Each unit typically comprises a pair of bipolar electrodes. For some applications, both bipolar electrodes (+ and −) in each unit protrude from array 90 and are configured to penetrate tissue of retina 6. One of these electrodes may be stimulating, and the other a return electrode, or else both may be stimulating. For some applications, the stimulating electrode is longer than the return electrode in each pair, and reaches the layer of bipolar cells, while the shorter return electrode only reaches the NFL layer. For other applications, one electrode (either the + or the −) protrudes from array 90 and is configured to penetrate tissue of retina 6, and the other electrode, of opposite polarity, is a surface electrode that is not configured to penetrate tissue of retina 6, but rather functions as a return electrode. The distance D1 between the pair of bipolar electrodes 64 in each unit is typically between 5 and 50 um, e.g., 10 um. The distance D2 between electrodes of adjacent units is typically between 25-100 um, e.g., 50 um. Generally, the distance D1 between a pair of electrodes in each unit is smaller than (e.g., less than half of) the distance D2 between electrodes of adjacent units.

Reference is made to FIGS. 1 and 2A-B. As shown in FIG. 2B, which is a Z view from the distal tip 72 of electrodes 64, the major axis W1 of base portion 66 of insulated portion 68 is typically 1.5-2.5 (e.g., 2) times larger than the minor axis W2 of body portion 65. Typically, major axis W1 is 25-200 um, e.g., 50-150 um (e.g., 100 um), and minor axis W2 is 10-100 um, e.g., 20-80 um (e.g., 50 um)

Reference is again made to FIGS. 1 and 2A-B. As mentioned hereinabove, for some applications, electrodes 64 comprise bipolar electrodes that are configured to penetrate retinal tissue of a subject. Penetrating bipolar electrodes, which are typically implanted such that both the stimulating and return electrodes are in close proximity to a neuronal retinal cell, require a smaller potential between the electrodes and enable reaching a higher potential drop across a given cell, resulting in enhanced stimulation of the cell. This is in contrast to many epi-retinal implants known in the art in which neuronal cells of the retina are stimulated by a surface electrode on the ILM layer.

For some applications, an array 90 of electrodes 64 is divided into subsets of electrodes. For such applications, a subset of three or more, e.g., 3-6, stimulating electrodes, by way of illustration and not limitation, surround and share a common return electrode 8. Each electrode in the subset receives a signal, through driving circuitry, from a discrete, respective, photosensor in support substrate 62, and in response, stimulates the retina of the subject. In such applications, the return electrode typically has a sufficiently large surface area in order to accommodate the electric charge returning from the subset of stimulating electrodes. Generally, such an arrangement of array of electrodes 64 enables the use of a reduced number of electrodes, since several stimulating electrodes share a common return electrode. For some applications, the stimulating electrodes are configured to drive electrical charges into the cells of retina non-simultaneously. Such staggering of the driving of each electrode in the subset reduces the amount of return electrical charge that is driven through the return electrode at a given time. For some applications, array 90 comprises at least 10 subsets of electrodes, e.g., 100-500 subsets. For some applications, array 90 comprises 500-1500 subsets of electrodes.

Reference is again made to FIGS. 2A-B. Electrodes 64 are typically fabricated by conventional fabrication processes known in the art. For some applications, following fabrication, electrodes 64 are assembled on array 90 by methods such as "pick and place." For other applications, other methods are used to fabricate array 90 of electrodes 64, e.g., three dimensional etching and/or MEMS Palladium etching technique. For some applications, techniques described in one or more of the following patents are practiced in combination with techniques and apparatus described herein: U.S. Pat. No. 7,096,568, U.S. Pat. No. 6,678,458, U.S. Pat. No. 6,923,669, U.S. Pat. No. 6,473,365, U.S. Pat. No. 6,762,116 U.S. Pat. No. 7,025,619, U.S. Pat. No. 7,081,630 and U.S. Pat. No. 6,677,225 which are incorporated herein by reference.

Figure 3:
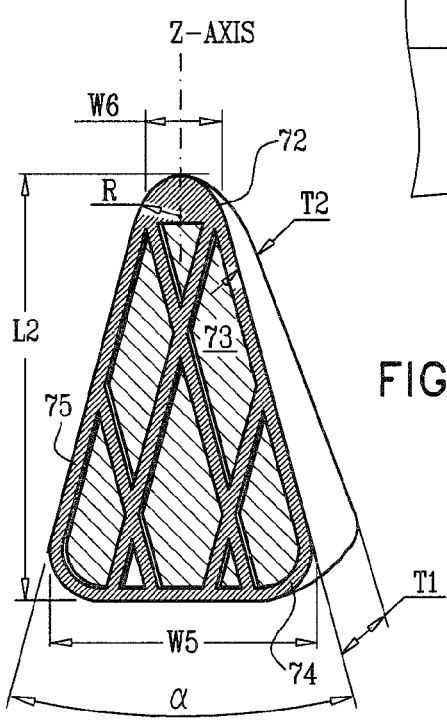
FIG. 3 is a schematic cross-sectional illustration of a pointed tip an of electrode, in accordance with some applications of the present invention.

Reference is now made to FIG. 3, which is a schematic cross-sectional illustration of a tip portion 70, in accordance with some applications of the present invention. Intraocular device 60 comprises electrodes which, for some applications, are shaped to define respective pointed tips configured for penetrating tissue of the subject. Each tip 70 is typically an electrically exposed tip, configured to directly drive electrical charge into the retinal tissue, e.g., bipolar cells, causing stimulation of the tissue and resulting in enhanced vision. Exposed tip 70 of the electrode typically has a length L2 of between 25 um and 100 um, e.g., 50 um. Typically, although each tip 70 is pointed when viewed from a distance, and thus functions as a pointed tip for purposes such as penetrating tissue, a close examination of the tip 70 reveals that it is shaped to have a radius of curvature R of 0.5-10 um, e.g., 2 um.

Tip 70 may be shaped to define a tip having an angle alpha of 30-60 degrees. As shown in FIG. 3, tip 70 comprises a tip-base portion 74 and a distal tip 72. Base portion 74 of tip 70, which is at a distal end of the electrode body portion, has a width W5 of between 15 um and 60 um, e.g., 30 um. Tip 70 typically decreases monotonically in width along its longitudinal axis from tip-base portion 74 to distal tip 72, until it reaches a width W6 of between 1 um and 20 um, e.g., 10 um, 4 um proximal from distal tip-end 72. For some applications, tip 70 is reduced in size after electrode shaping by techniques such as laser ablation.

As shown in FIG. 3, tip 70 typically decreases monotonically in thickness along its longitudinal axis from base portion 74 to distal tip 72. Base portion 74 of tip 70 has a thickness T1 of between 5 um and 20 um, e.g., 10 um. Distal tip 72 of tip 70 has a thickness T2 of between 0.5 um and 5 um, e.g., 2 um. The shape of the distal tip of tip 70, and a radius of curvature R of tip 70, typically reduces the extent to which tip 70 penetrates and/or ruptures cells with which it comes in contact. Typically, retinal neuronal cells range between 5 and 10 um. Radius of curvature R is typically 0.5 um-10 um, e.g., 2 um, roughly in the same magnitude as the cells. Generally, all edges of electrode tip 70 and electrode 64 have a radius of curvature that is greater than 0.1 um, e.g., greater than 0.5 um. Rounding of the edges is typically done to reduce concentration of charge at sharp edges. Surface treatments to increase roughness of a surface of tip 70, as described hereinbelow, are also used to smoothen and round edges of tip 70 and electrode 64.

Typically, tip 70 of electrode 64 is treated to increase surface roughness of tip 70. For some applications, an area 73 of tip 70 is treated to increase roughness, whereas another area 75 of tip 70 remains untreated in order to maintain structural strength of the tip.

Reference is made to FIGS. 2A-B and 3. As shown in FIG. 3, untreated areas 75 are maintained in order to strengthen tip 70 for withstanding compression forces applied during penetration of tip 70 into retinal tissue. Surface treatment of the tip in areas 73 typically affects an area of the tip that is as deep as 2 um from the surface. Increased surface roughness causes an increased surface area of the tip. The tip is treated to increase roughness such that 1 mm2 area has an equivalent surface area of between 10 mm2 and 1000 mm2, e.g., 100 mm2. Increased surface area generally reduces electrode impendence, thereby enhancing stimulation of retinal tissue by electrodes 64. Additionally, increased roughness generally reduces surface charge density and improves electrode capacitance, enabling an increase in the charge injection limit. Increased surface roughness to reduce charge density is typically achieved by techniques of nanofabrication and/or metal etching, as described in Lianga, 2008 (referenced hereinabove).

For some applications, electrodes 64 are coated with carbon nanotubes. Typically, carbon nanotubes create a rough surface in electrode 64, including tip portion 70. Rough surfaces in general and carbon nanotube surfaces in particular have been shown to attract neurons and promote neuronal growth. As described in Sorkin et al., 2009 (referenced above) neurons were found to bind and preferentially anchor to carbon nanotube rough surfaces. Thus, adhesion of retinal neurons, e.g., bipolar cells, to carbon nanotube electrodes provided by these applications of the present invention, promotes cell-electrode coupling and/or axon regeneration, leading to improved stimulation of the retina. For some applications, the carbon nanotube coating of electrode 64 is glued to the electrode surface and/or grown on a selected surface of the electrode by using doping techniques known in the art.

For some applications, a femtosecond laser is used to increase surface roughness of electrodes 64. Femtosecond laser treatment produces rough surface structures on titanium possibly for the use of implants and other biomedical applications treatments (Vorobyev et al., 2007 referenced above). As described in Vorobyev et al., femtosecond laser treatment increases the roughness of a titanium substrate in the range of 1-15 um. Additionally, femtosecond laser treatment was shown to produce a variety of surface nanostructures, such as nanoprotrusions and nanopores on the titanium substrate. Liang et al., 2007, (referenced above), report good bioactivity of a pure titanium substrate that was treated with a femtosecond laser to increase roughness of its surface.

For some application, a blanket etch MEMS procedure is used to increase surface roughness of electrodes 64. For such applications, the entire electrode 64 is blanketed and tip 70 is etched to increase surface roughness and achieve a desired aspect ratio in a similar procedure to that described in U.S. Pat. No. 6,770,521 to Visokay.

Figure 4A:
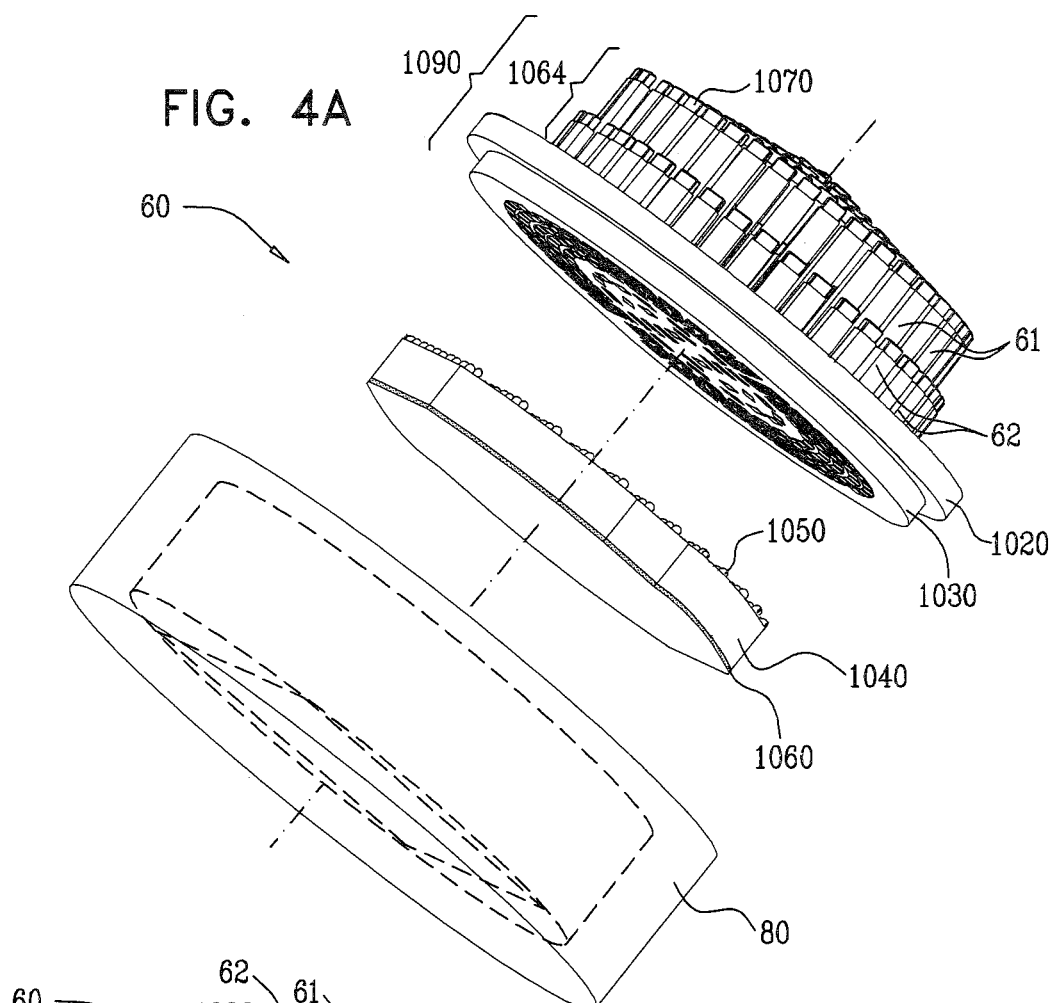
FIGS. 4A-B are schematic illustrations of an intraocular device for retinal stimulation, in accordance with some applications of the present invention.
Figure 4B:
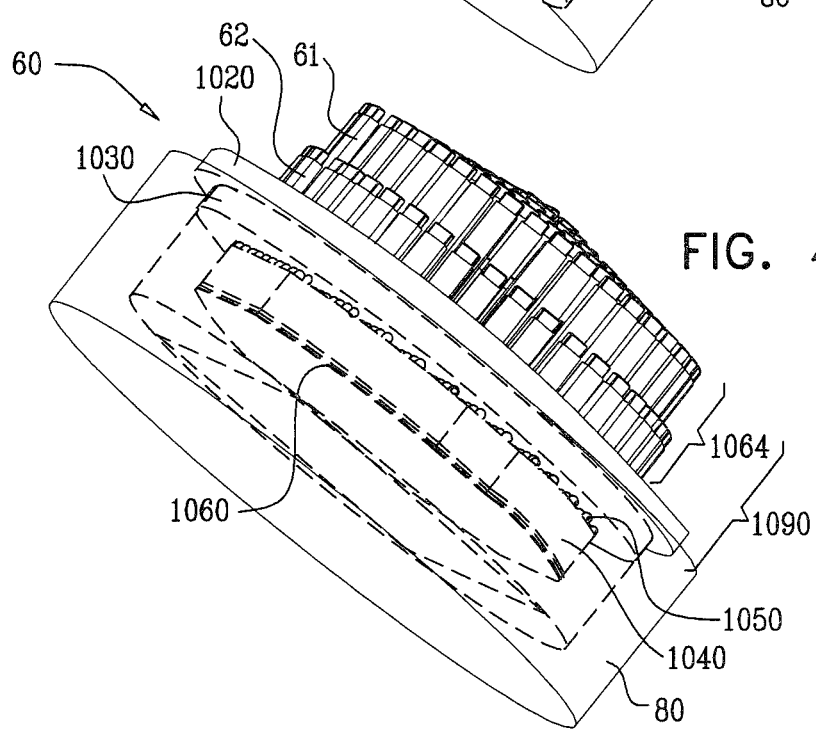

Reference is made to FIGS. 4A-B, which are schematic illustration of intraocular device 60, in accordance with some applications of the present invention. Device 60 typically comprises an array 1090 of protruding electrodes 1064 configured to penetrate the retina of a subject. It is to be noted that techniques and apparatus described herein with reference to electrodes 64 and array 90 apply to electrodes 1064 and array 1090, and vice versa, except where otherwise indicated. For some applications, electrodes 1064 vary in length. Electrodes 61 are generally longer than electrodes 62, thereby facilitating direct stimulation of distinct areas of the retina, e.g., layer of the bipolar cells and/or the layer of ganglion cells. Other dimensions of the electrodes are described hereinbelow, with reference to FIG. 6.

Electrodes 1064 comprise any suitable material e.g., palladium and/or titanium, and/or silicon electrodes. For some applications, electrodes 1064 comprise a metal alloy and/or doped electrodes. Typically, a silicon wafer 1030 forms the base of array 1090 from which electrodes 1064 protrude. For some applications, wafer 1030 is selectively etched to a desired depth by using any suitable technique known in the art, e.g., techniques of Deep Reactive Ion Etching (DRIE). For some applications, following bonding of the silicon wafer, electrodes 1064 are etched by using any suitable technique known in the art, e.g., techniques of Deep Reactive Ion Etching (DRIE), to have desired dimensions and aspect ratios. For some applications, additional metals such as platinum, and/or palladium, are deposited on electrodes 1064 by using, for example, a shadow mask technique. An attaching titanium ring frame 1020 is typically electroplated with electrodes 1064 to form structure that can subsequently be welded to the metal ring case 2020 (shown in FIG. 5). The silicon wafer 1030 is typically biocompatible. Ring frame 1020 is typically bonded to silicon wafer 1030, by using, e.g., fusion bonding. Suitable fusion bonding techniques are described in an article by Jourdain et al., entitled, "Fabrication of piezoelectric thick-film bimorph micro-actuators from bulk ceramics using batch-scale methods," which is incorporated herein by reference. Wafer 1030 typically comprises through-wafer vias.

Typically, device 60 additionally comprises a CMOS chip 1040 including through-silicon vias. For some applications, solder bumps 1050 are deposited on an upper side of CMOS chip 1040, electrically connecting chip 1040 to silicon wafer 1030. Additionally, for some applications, device 60 comprises a layer 1060. Layer 1060 typically comprises additional elements of an intraocular retinal prosthesis, e.g., an energy receiving layer, a photosensor layer and driving circuitry that is powered by the energy receiving layer. The driving circuitry typically drives electrical charge into the retinal tissue from the rough tips 1070 of electrodes 1064, in response to sensing by the photosensor layer, in order to stimulate the retinal tissue. The electrical signal generated by layer 1060 is typically routed through silicon wafer 1030 to electrodes 1064, providing sealing on one side and electrical contact on the other.

For some applications, a back side of the titanium wafer is bound to a glass cap 80 which, as shown in FIG. 4B, encapsulates the entirety of intraocular device 60, excluding array 1090 of protruding electrodes 1064. For some applications, glass cap 80 comprises two distinct glass pieces, one of which is shaped to define a hole. The glass pieces are typically bonded to each other by anodic bonding, forming a single glass cap 80. Bonding of titanium frame 1020 to glass cap 80 is optionally done using thermal compression bonding. This low temperature bonding step generally does not affect circuitry of intraocular device 60. Glass cap 80 generally reduces exposure of human tissue to any toxic materials, e.g., contaminated silicon, which may exist in intraocular device 60. Typically, laser welding is used to close the glass encapsulation.

Figure 5:
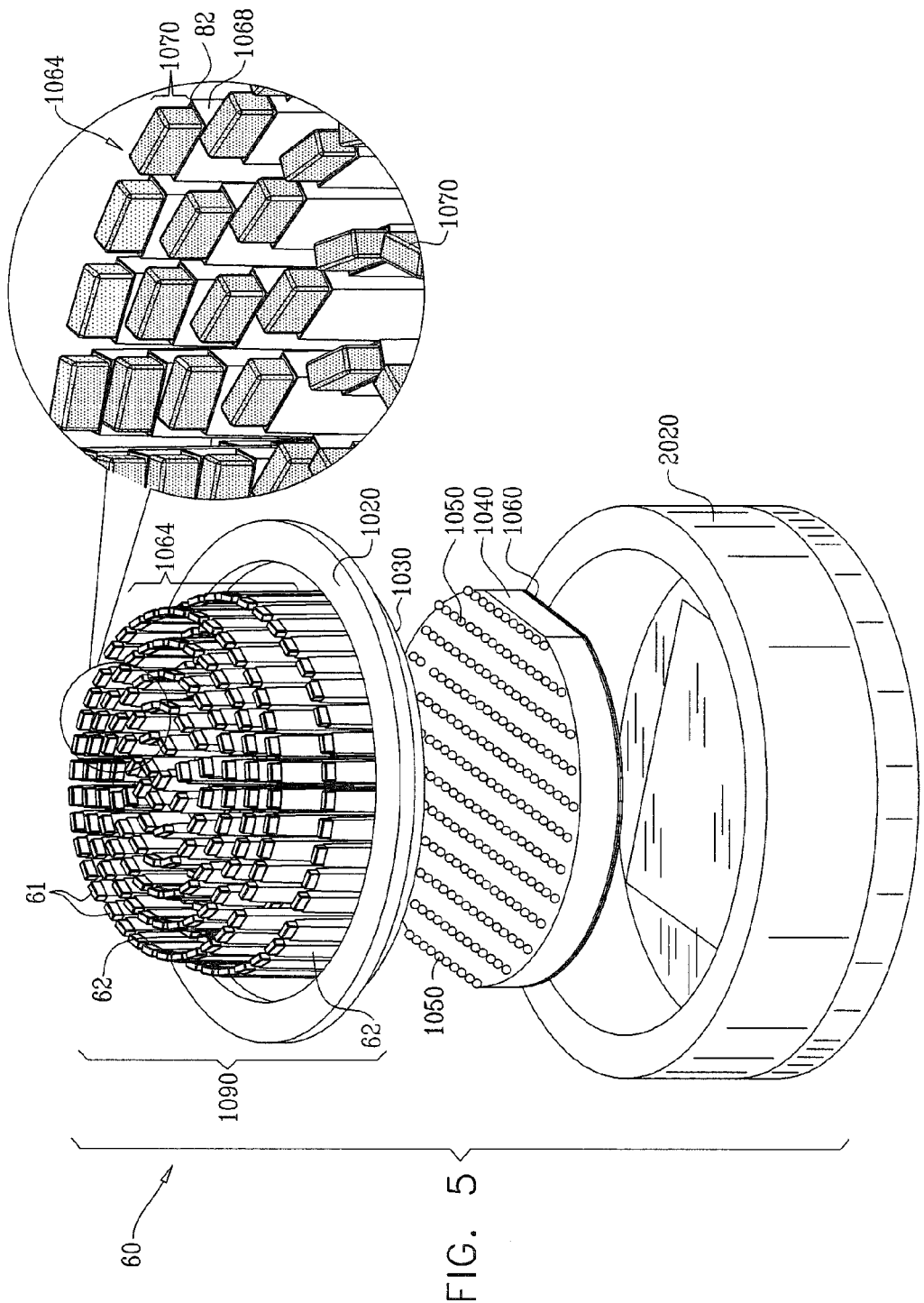
FIG. 5 is a schematic illustration of an intraocular device for retinal stimulation, in accordance with some applications of the present invention.

Reference is made to FIG. 5, which is a schematic illustration of intraocular device 60, in accordance with some applications of the present invention. As described hereinabove, intraocular device 60 typically comprises array 1090 of electrodes 1064, which are configured to penetrate retinal tissue of a subject. For some applications, electrodes 1064 comprise long electrodes 61 and short electrodes 62. Array 1090 is typically bonded to silicon wafer 1030 which is coupled to CMOS chip 1040 via solder bumps 1050. As shown in FIG. 5, for some applications, intraocular device 60 comprises a metal ring 2020 which encapsulates the entirety of intraocular device 60, excluding array 1090 of protruding electrodes 1064. For some applications, metal ring 2020 functions as DC grounding for electrodes 1064. Additionally, in a case in which an electrode is not active, it may be held to ground by activating a switch that locks the electrode to metal ring 2020, such that the electrode stays at ground.

Reference is now made to FIGS. 1 and 5. As described hereinabove with reference to FIG. 1, each electrode in intraocular device 60 comprises an electrically-insulated body portion coupled to an electrically exposed distal tip. FIG. 5 shows an exploded view of electrodes 1064 showing body portion 1068 of electrodes 1064 coated with a polyimide insulating coating 82. Tip 1070 of electrode 1064 remains electrically exposed, i.e., not coated with a polyimide coating, to enable an electrical connection between the tip and the bipolar layer (or other portions of the retina). As described hereinabove, in some applications, tip 1070 physically contacts the layer of bipolar cells 14 when intraocular device 60 is implanted in the eye of a subject. For some applications, the entire electrode is fabricated to include a polyimide coating, followed by for example, an etching process to selectively remove the polyimide coating from electrode tip 1070. Alternatively, the polyimide coating is removed from the tip 70 by laser ablation. Seo et al. (2004) (referenced hereinabove) report that polyimide is a suitable material for a retinal prosthesis.

As described hereinabove with reference to FIG. 3, the electrically exposed tips of the electrodes are treated to increase surface roughness. Accordingly, FIG. 5 shows tip 1070 having a rough surface to increase neuronal cell adhesion to tip 1070, thus increasing tissue stimulation by electrodes 1064. Typically, tip 1070 is configured to penetrate retinal tissue of a subject.

Typically, intraocular device 60 is configured to match the natural curvature of the retina to facilitate implantation and anchoring of intraocular device 60 to the retina. Accordingly, electrodes 1064 typically vary in length, and as indicated by FIGS. 4A-B and 5, for some applications, tips 1070 of electrodes 1064 together define a convex curved surface having a radius of curvature that is 6-15 mm.

Figure 6:
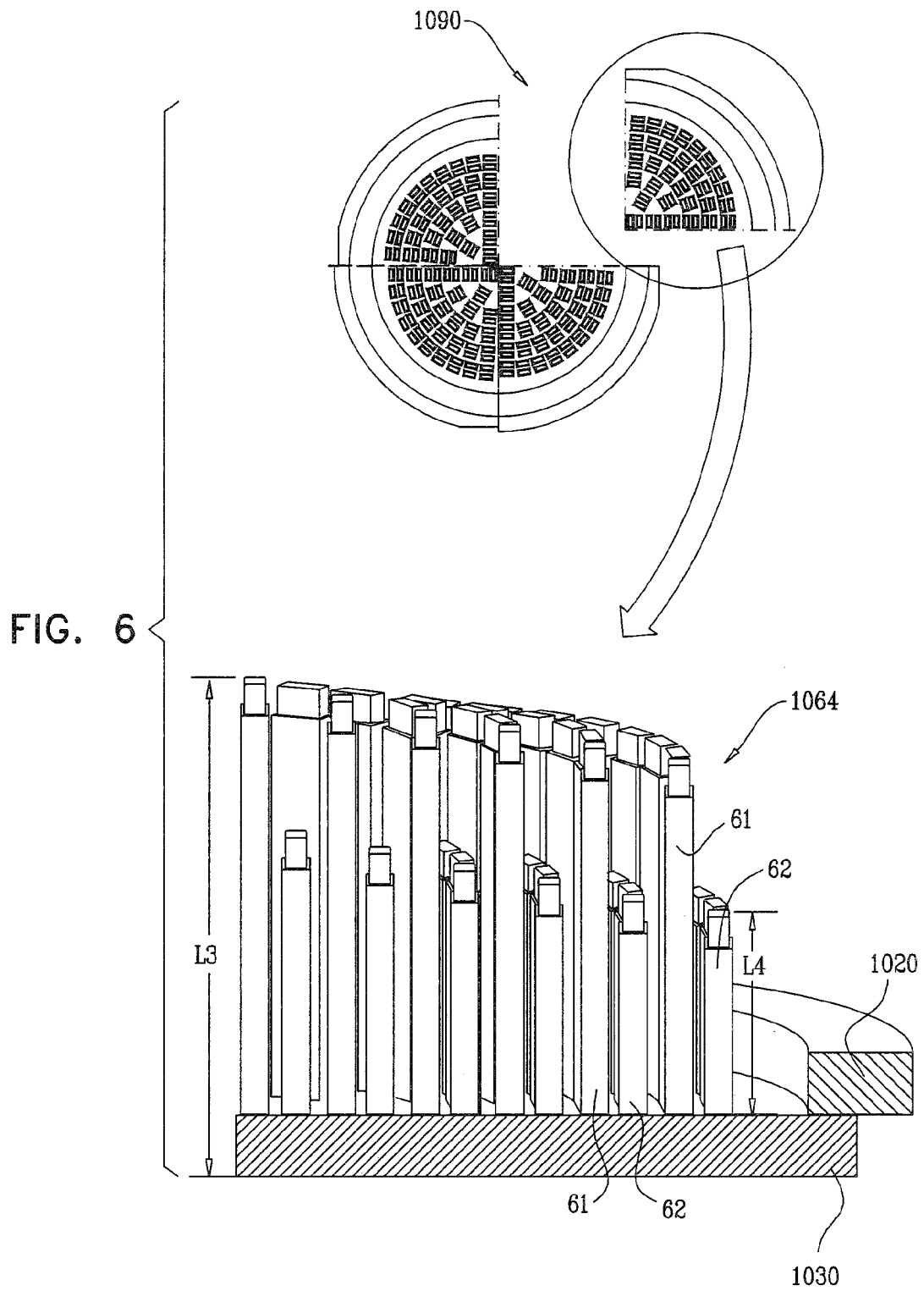
FIG. 6 is a schematic illustration of an array of penetrating electrodes, in accordance with some applications of the present invention.

Reference is made to FIG. 6 which is a schematic illustration of a section of array 1090 of electrodes 1064, in accordance with some applications of the present invention. As shown, array 1090 typically comprises electrodes 1064 of varying heights. For some applications, electrodes 1064 are arranged in concentric circles on wafer 1030. The circles of electrodes 1064 typically alternate between long electrodes 61 and short electrodes 62, such that electrodes 1064 are typically arranged in pairs of bipolar electrodes. Each pair of electrodes typically comprises a single long electrode 61 and a single short electrode 62.

Intraocular device 60 and electrodes 1064 are typically configured to match the natural curvature of a human organ and/or tissue in which it is implanted, e.g., the retina. As shown in FIG. 6, for some applications, electrodes 1064 vary in length. Electrodes 61 are generally longer than the electrodes 62, thereby facilitating direct stimulation of distinct areas of the retina, e.g., layer of bipolar cells and/or the layer of ganglion cells. For some applications, long electrodes 61 have a length L3 of 200-800 um, e.g., 300-500. Short electrodes 62 typically have a length L4 of 100-550 um, e.g., 150-350. Typically long electrodes 61 are 50-150 um longer than the adjacent short electrodes 62. For some applications, both long electrodes 61 and short electrodes 62 function as stimulating electrodes. For other applications, long electrodes 61 function as stimulating electrodes and short electrodes 62 function as return electrodes. For some applications, return electrodes 62 are less than 10 um in length, and may even comprise surface electrodes. In this case, L4 is less than 5 um in length.

Figure 7:
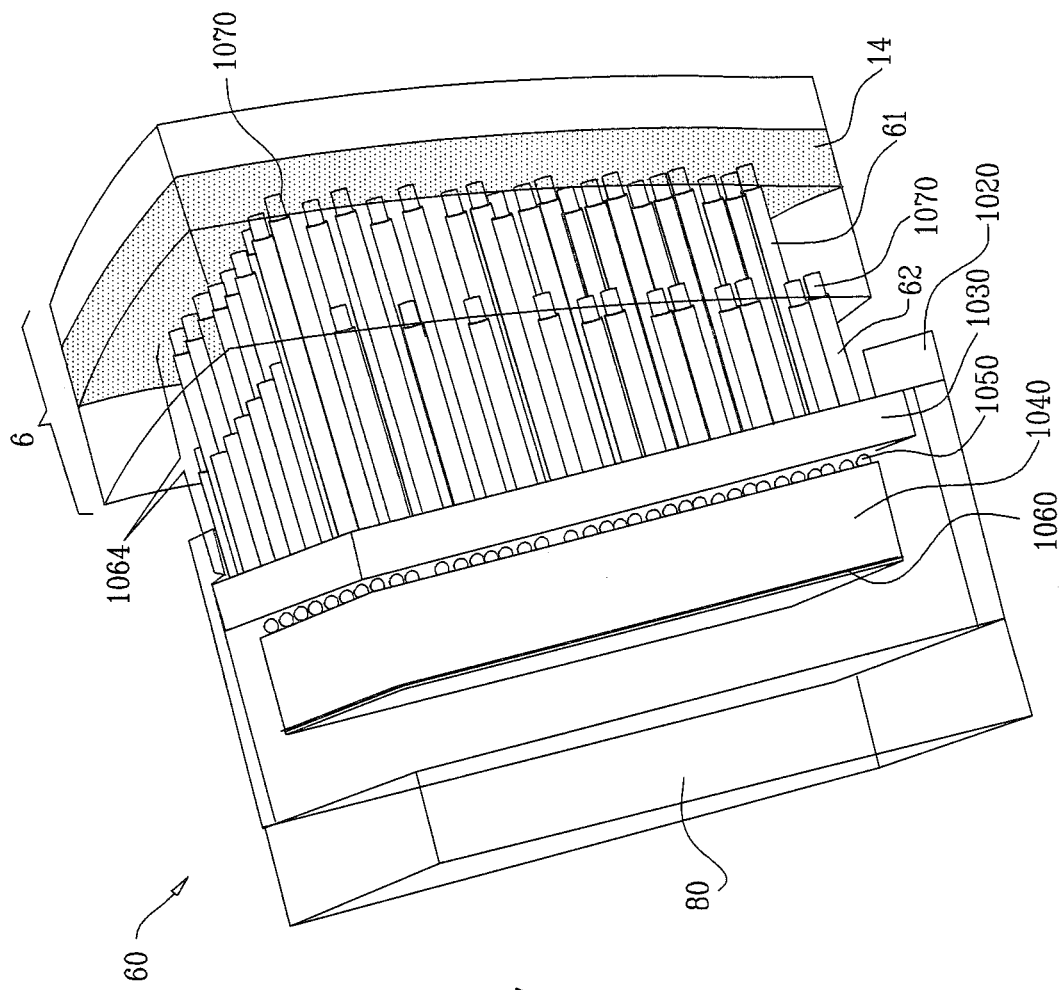
FIG. 7 is a schematic illustration of an intraocular device penetrating retinal tissue, in accordance with some applications of the present invention.

Reference is made to FIG. 7, which is a schematic illustration of device 60 disposed in retina 6, in accordance with some applications of the present invention. FIG. 7 shows components of device 60 (silicon wafer 1030, attaching ring frame 1020, CMOS chip 1040, solder bumps 1050 and layer 1060) in glass encapsulation 80. Electrodes 1064 are shown penetrating retina 6. For some applications, and as described hereinabove with reference to FIG. 6, electrodes 1064 of intraocular device 60 are arranged in pairs of bipolar electrodes. For some applications, both bipolar electrodes (+ and −) of each pair protrude from intraocular device 60, and are configured to penetrate tissue of retina 6. For some applications, the electrodes in each pair are of varying lengths, such that one electrode (either the + or the −) is longer than the second electrode. Typically, the longer electrode 61 (e.g., 200-800 um in length) is configured to protrude from intraocular device 60 and penetrate retinal tissue in order to contact and stimulate the bipolar cell layer. The shorter electrode 62 (e.g., 100-550 um in length) is typically configured to protrude from intraocular device 60 in order to contact and stimulate epi-retinal tissue, e.g., the NFL layer. Additionally or alternatively, short electrode 62 is configured to penetrate and stimulate retinal ganglion cells. For some applications, long electrodes 61 function as stimulating electrodes, e.g., to stimulate the bipolar cells and short electrodes 62 function as return electrodes.

For other applications, one electrode (either the + or the −) protrudes from intraocular device 60 and is configured to penetrate tissue of retina 6, and the other electrode, of opposite polarity, is a surface electrode that is not configured to penetrate tissue of retina 6, but rather functions as a return electrode (application not shown). Typically, intraocular device 60 comprises at least 100 short or surface electrodes, and at least 400 long electrodes.

For some applications, electrodes 1064 comprise hook electrodes configured to anchor to retinal tissue of a subject, increasing coupling between the target cells and the electrode.

Reference is made to FIGS. 1-7. For some applications, intraocular device 60, including substrate 62, is flexible and can be adjusted to match the natural curvature of the retina during implantation. Intraocular device 60 may be adjusted to match the retina of a subject by standard fitting and/or can be tailor made according to OCT imaging of the retina. Once adjusted to match the natural curvature of the retina, intraocular device 60 is typically glued and/or stitched in place. For other applications, intraocular device 60 is generally rigid, and electrodes of varying heights and, optionally, shapes enable proper attachment of the intraocular device to the curved structure of the retina.

Reference is again made to FIGS. 1-7. It is to be noted that a plurality of implantable devices 60 may be implanted in discrete locations in tissue of retina 6, either arranged in an array, or, for example, pseudo-randomly. Typically, intraocular device 60 is wireless and does not comprise bulky components, facilitating implantation of several implants 60 in retina 6 of the subject.

It is to be noted that a system comprising penetrating electrodes with rough and/or perforated tips as described hereinabove with reference to FIGS. 1-7, may be implanted in any other organ (e.g., brain, nose, ears and/or tongue), and used in any other neurological application (e.g., cortex stimulation). Implantation of penetrating electrodes as described hereinabove in, for example, brain tissue of a subject typically reduces the amount of power required to stimulate the tissue. Additionally or alternatively, implantation of such electrodes facilitates specific sensing and enhances specific stimulation of a target neuron in the tissue by directly contacting selective areas with the electrodes.

For some applications, a system comprising penetrating electrodes as described hereinabove may be used to stimulate organs such as the liver or the pancreas. Implanting an array of such electrodes in, for example, selected areas of pancreatic tissue (e.g., insulin-secreting areas) enables specific and more effective stimulation of these areas.

Reference is again made to FIG. 4. For some applications, layer 1060 is a multilayer array comprising an energy receiving layer, a photosensors layer and driving circuitry that is powered by the energy receiving layer. The driving circuitry typically drives current into the stimulating electrodes 1064, in response to sensing of ambient light by the photosensor layer, in order to stimulate the retinal tissue. Alternatively, layer 1060 comprises a single layer array configured both for energy receiving and photosensing. For some applications a portion of the single array is configured for energy reception and a separate portion of the array is configured for photosensing. Alternatively, for applications in which a single layer is configured both for energy receiving and photosensing, the entire layer is configured, during alternating time periods, to (a) receive energy from power source 24 (shown in FIG. 1) to power the driving circuitry, and (b) sense ambient light and responsively transmit a signal to the driving circuitry.

Reference is made to FIG. 8, which is a block diagram of the transmission of energy, information, and instructions, in system 20, in accordance with some applications of the invention. External device 600 is located outside of a body of a subject and comprises power source 24, which emits energy to power components of intraocular device 60. The energy which is transmitted to device 60 is received by energy receiver 32. Energy receiver 32 typically comprises a voltage regulator 29 configured to maintain a constant voltage level to power the components of device 60. Intraocular device 60 further comprises photosensors 34 configured to detect photons 33 and generate a photosensor signal responsively to the photons. For some applications, a single light receiving element indicated by box 210 functions, during alternating time periods, as an energy receiver 32 and photosensors 34. The photosensor signal is transmitted to driving circuitry 36, which drives the electrodes 1064 to apply electrical charges to cells of retina 6. As shown, system 20 typically comprises a control unit 200 configured to regulate operating parameters of intraocular device 60. For example, the control unit may regulate operation of photosensors 34.

Typically, photosensors 34 are arranged as an array of photosensors 34. In some configurations of device 60, each photosensor in the array of photosensors corresponds to a stimulating electrode in the array of electrodes 1064. For some applications, each photosensor functions independently, i.e., each photosensor receives photons 33 and in response sends signals to driving circuitry 36, whereupon the driving circuitry drives the corresponding electrode to apply electrical charge to the retina 6. Thus, intraocular device 60 comprises an array of photosensor units, each photosensor unit comprising a photosensor and a corresponding electrode. Accordingly, the degree of retinal stimulation applied by each photosensor unit in the intraocular device is dictated by the light received by that unit. For some applications, each photosensor unit translates the level of light received by that unit into a train of stimulation pulses that is applied to the retina by the electrode. Additionally, such conversion of intensity of received light to frequency of stimulation can include a log transformation, such that for example: x photons received by the photosensor unit translate into one stimulation pulse applied by the electrode, while 10× photons correspond to only 2 stimulation pulses applied by the electrode.

Although functioning independently from one another, for some applications, a central control unit 200 regulates the function of each photosensor and corresponding electrode unit. Additionally or alternatively, each photosensor unit is configured to communicate with other units located in close proximity, and to modulate the electrical charge it drives into the retina in response to the functioning of neighboring units. Regulation of the electrical charge applied by each unit in the array of photosensors 34 with respect to other units in the array facilitates regulation of diverse features of visual perception. Varying the electrical charges applied to retinal neurons allows improved processing of the electrical charge by the retinal neurons e.g., bipolar cells.

For some applications, processing is performed by control unit 200. In some configurations of intraocular device 60, there is a larger number of photosensors than stimulating electrodes. For example, processing by control unit 200 can include disabling a bad pixel, improving focus of an image, sharpening, level adjustment, edge enhancement, and motion detection. Typically, this is performed using the data provided by the significantly larger number of photosensors than stimulating electrodes. Thus, edge detection and enhancement (or other image processing techniques) are performed using the hundreds of data points (or more), which are available to the control unit after having been sampled by the individual photosensors. This processing is used to allow the smaller number of stimulating electrodes to apply a more meaningful form of retinal stimulation, which reflects the output of the image processing (e.g., by showing an enhanced edge, emphasizing motion, or sharpening individual elements of an image). The scope of the present invention includes performing any of the image processing techniques described herein, even if the number of photosensors is not smaller than the number of stimulating electrodes. For some applications, a standard process is utilized in order to, e.g., enhance sensitivity by summation, edge detection for a clearer image, noise reduction in time and space, and/or adaptive dynamic range. Alternatively, the control unit facilitates processing, such as edge enhancement, by horizontal and/or amacrine cells of the retina, by providing a simpler image than that imaged by the photosensors. This simpler image is more easily processed by the retina neuron network.

For some applications, intraocular device 60 comprises protruding electrodes which are sufficient in length to contact bipolar cells 14 (shown in FIG. 1), thereby directly driving electrical charges into the bipolar cells. Thus, the electrical charge from the electrodes is directly driven into the bipolar cells, which transmit the viewed image via the ganglion cells and the optic nerve to the brain. Additionally, other retinal neurons, e.g., horizontal cells and/or amacrine cells, perform image processing to enhance and improve the received image. Examples of such processing include: focusing, edge detection, light adjustment, averaging, and motion detection. By directly contacting the layer of bipolar cells, device 60 mimics the natural transferring of a signal from native photoreceptor cells directly to the bipolar cells, for processing by the bipolar cells. The photoreceptor nerve cells are typically connected by synapses to bipolar nerve cells, which are then connected to ganglion nerve cells 12. The ganglion nerve cells connect to the optic nerve fibers, which carry the information generated in the retina to the brain.

For some applications, device 60 may comprise protruding electrodes that are shorter in length (e.g., 50-200 um, e.g., 100-150 um) and configured to directly contact the layer of ganglion cells 12 (shown in FIG. 7). For some applications, control unit 200 is configured to perform processing of the signals from the photosensors, and directly apply the pre-processed electrical charges via the electrodes to the ganglion cells, e.g., as described hereinabove with respect to improving edge detection or other image processing techniques.

Reference is again made to FIG. 8. For some applications, central control unit 200 regulates the function of some or all photosensors 34 and their corresponding electrode(s) 1064, e.g., by controlling the duration of a sensing period of each photosensor. Typically, the amount of ambient light that lands on the array of photosensors is used by the central control unit to determine the duration of a sensing period of each photosensor, i.e., the amount of time in which the photosensor receives photons before the driving circuitry drives the corresponding electrode to drive electrical charge into retinal tissue (e.g., 0.1 ms-30 ms). Thus, for example, the sensitivity of each photosensor may be increased over the course of several seconds, if the subject enters a dark room.

Additionally or alternatively, central control unit 200 sets the duration of an energy receiving period, i.e., the amount of time in which energy receiver 32 receives energy from external power source 24 before that energy is passed to driving circuitry 36 to drive the electrodes to drive electrical charges into retinal tissue (e.g., 1-10 ms, or 10-100 ms). For example, control unit 200 may increase the duration of an energy receiving period to supply device 60 with a sufficient amount of energy, e.g., if the subject increases the intensity such that a larger amount of electrical charge is applied through the electrodes, resulting in device 60 requiring an increased amount of energy. Further additionally or alternatively, central control unit 200 regulates the stimulation timing.

Reference is still made to FIG. 8. For some applications, in addition to supplying power to device 60, the energy emitted by power source 24 is used to regulate operation of intraocular device 60. This regulation may be in real-time, e.g., where the duration of each laser pulse corresponds to the duration of stimulation applied by an electrode to the retina. Alternatively, this regulation is not in real-time, e.g., conveying a digital message to the controller, which, in turn, modulates the stimulation signal (for example to increase exposure time). In some applications, external device 600 comprises a control element 27 (e.g., a dial, switch, or button) coupled to eyeglasses 25 (shown in FIG. 1), allowing the subject to interactively control the intensity of the electrical charge applied to retina 6 and/or the sensitivity of photosensors 34 to received light, and/or another system parameter. Typically, the intensity of the electrical charge applied to the retina by the electrodes is determined by driving circuitry 36, which drives electrodes 1064 to apply the electrical charge in pulses of electrical charge. The driving circuitry is configured to alter the intensity of electrical charge applied to the retina by regulating a stimulation parameter such as a number of the pulses, a frequency of the pulses, duration of each pulse, or a pulse repetition interval of the pulses. Additionally or alternatively, the driving circuitry is configured to control amplitude of the electrical charges applied by the electrodes. Control unit 200 is configured to regulate the function of the driving circuitry to adjust the intensity of the electrical charge based on the subject's input. Additionally, for some applications, the sensitivity of photosensors 34 to received light is determined by the duration of a sensing period of photosensors 34. Control unit 200 is configured to increase or decrease sensitivity of device 60 in response to the subject's input, e.g., by regulating the duration of a sensing period.

For example, if the subject determines that the overall stimulation being applied by device 60 to the retina is too strong, then he can adjust a setting on the control element to reduce the stimulation strength. Similarly, if he senses that his entire visual field is over-stimulated, indicating that the sensitivity of photosensors 34 is too high (e.g., resulting in the entire array of electrodes activating the retina at high intensity), then he can adjust another setting on the control element to reduce the sensitivity. In response to the subject's input, the energy emitted by the power source is modulated to regulate operating parameters of device 60, e.g., to increase or decrease intensity and/or sensitivity. An example of a suitable modulation protocol includes a first train of six short pulses from power source 24, indicating that stimulation intensity is going to be changed, followed by a train of between one and ten longer pulses indicating a subject-selected desired level of stimulation intensity. To change sensitivity, a first train of six long pulses is emitted from power source 24, followed by a train of between one and ten longer pulses indicating a subject-selected desired level of sensitivity. A person of ordinary skill in the art will appreciate that other encoding protocols may be used, as well.

Typically, central control unit 200 receives modulated energy from energy receiver 32, and demodulates the energy to regulate operation of device 60 accordingly. For example, based on the subject's input, the energy emitted by power source 24 is modulated to signal to device 60 to decrease or increase sensitivity of photosensors 34. (For example, the modulation may include changes in pulse timing of pulses emitted by power source 24.) Control unit 200 is configured to demodulate the energy received by energy receiver 32 and, for example, accordingly determine the duration of a sensing period of the photosensors, i.e., the amount of time in which the photosensors receive photons before the driving circuitry drives the corresponding electrode to drive electrical charge into retinal tissue (e.g., 0.1 ms-5 ms, or 5 ms-100 ms). This thereby increases or decreases the sensitivity of the photosensors according to the subject's input. Additionally or alternatively, control unit 200 is configured to demodulate the energy received by energy receiver 32 and accordingly regulate the driving circuitry to alter the intensity of electrical charge applied to the retina by altering a stimulation parameter such as a number of the pulses, a frequency of the pulses, duration of each pulse, and a pulse repetition interval of the pulses.

Alternatively, the function of elements and/or arrays and/or sub-arrays of device 60 are controlled by several distributed control units.

For example, for some applications, each photosensor and corresponding electrode unit is controlled by an individual control unit which regulates system parameters, such as parameters of the photosensor. In an application, the sensitivity of the photosensors is regulated, for example, by setting the duration of a sensing period of each photosensor (i.e., the amount of time in which the photosensor receives photons before the driving circuitry drives the corresponding electrode to drive electrical charge into retinal tissue). For other applications, separate control units regulate the function of each subset of electrodes and corresponding photosensors.

Reference is made to FIGS. 1-8. For some applications, device 60 is configured to enable night vision (typically in addition to regular vision when there is sufficient light). Typically, photosensors 34 are sensitive to visible light and are configured to receive photons from ambient light and generate a signal in response thereto. For some applications, and in particular for conditions lacking ambient visible light, device 60 additionally comprises uncooled infrared (IR) detectors which receive incident IR radiation and produce an output signal depending on the amount of IR radiation landing on the detector. The uncooled IR detectors convert the incident IR radiation into an electrical current in device 60 which is conveyed to the driving circuitry, which in turn drives the electrodes to apply electrical charges to the retina, causing image formation.

Reference is again made to FIGS. 1-8. During implantation, device 60 is typically mechanically attached to the retina of a subject and/or glued into place.

Reference is still made to FIGS. 1-8, and in particular to FIG. 8B. For some applications, electrodes 1064 are arranged in several subsets 3002 of electrodes. For some applications, device 60 comprises N1 subsets, e.g., 10-2500 subsets, e.g., 100-500 subsets of electrodes. For some applications, array 1090 comprises 500-1500 subsets of electrodes. For some applications, each subset 3002 of electrodes comprises three or more electrodes. For some applications, an electrode in at least one of the subsets is within a distance D3 of another electrode in the subset, e.g., 300 um or 500 um of another electrode in the subset.

Typically each subset 3002 of electrodes shares a common power supply, e.g., a common capacitor 3004, which provides current (typically non-simultaneously) to all of the electrodes in a respective subset. In such applications, the capacitor in each subset is sufficiently large (e.g., 0.01-0.1 nf, or 0.1 nf-1 nf) to allow charging to less than 50% of full-charge of the capacitor during each charging of the capacitor. Using a large capacitor generally enhances the efficiency of intraocular device 60, since it allows for the capacitor to quickly recharge once it has provided currents to the electrodes. In contrast, using a single small capacitor in order to drive a single electrode typically requires a longer recharging period and is therefore less efficient. However, it is generally not possible to have one large capacitor per electrode, in an array of 100-1000 electrodes. As provided by some applications of the present invention, an array of several subsets of electrodes, in which each subset is driven by a respective common large capacitor, allows for the use of a reduced number of large capacitors, thus allowing the use of a large capacitor to drive a plurality of electrodes and thereby improving efficiency of the device.

For some applications, electrodes 1064 are arranged in subsets of stimulating electrodes which surround and share a common return electrode (as described hereinabove). At least some of the stimulating electrodes 1064 in each subset are configured to drive electrical charges into the neurons of the retina in non-simultaneous time periods. Consequently, for such applications, the common return electrode receives electrical charges from at least some of the stimulating electrodes in the subset non-simultaneously. Such staggering of the driving of each electrode and of the returning current generally reduces interference and neuron load. Such staggering also reduces tissue damage and/or prolongs the lifetime of the return electrode: Additionally, for applications in which the electrodes are arranged in subsets of electrodes, staggering of the driving of each electrode generally reduces the charge density per subset. Additionally or alternatively, staggering of the driving of each electrode generally reduces interference between adjacent neuron fibers, typically leading to improved sensation of vision.

For some applications, no dedicated return electrode is provided, but instead while one electrode in a subset drives electrical charges into the retina, some or all of the remaining electrodes in the subset act, collectively, as a return electrode.

Typically, application of electrical charges to the cells may be programmed such that generation of sub-harmonics and/or beat frequencies, and/or artificial frequencies and/or sensations of a flicker are reduced. For example intraocular device 60 may be configured to apply electrical charge through electrodes 1064 in a subset using changing sequences. For example, apparatus 60 may be configured to apply electrical charge through four electrodes in a subset using the sequence 1-2-3-4, followed by applying the electrical charge in a different sequence (3-1-2-4), by way of illustration and not limitation. Alternatively, the electrical charge is applied using time-based jittering of at least some of the electrical charge applications, to reduce the generation of sub-harmonics and/or beat frequencies, and/or artificial frequencies and/or sensations of a flicker. For example, instead of applying electrical charge pulses separated by a standard time gap, the time gap can be "jittered" by introducing a time variation in the frequency of these successive electrical charge pulses. Alternatively or additionally, other signal parameters may be jittered, such as pulse duration and amplitude. For some applications, a fuzzy logic, multi-value, concept is applied. For example, instead of having a single fixed parameter for power amplitude or jitter, the system has a range of each parameter and it will scan through this range in a regular or pseudorandom procedure. (In biological systems, the exact parameter that will produce an optimal response at any time is changing, but the range of the parameter is generally known.)

For some applications, system 20 is configured to restore at least some color vision in a subject suffering from damaged retinal photoreceptor cells, e.g., cones, by stimulating intact portions of the retina, e.g., the bipolar cells. Most cones lie in the fovea, which defines the center of the retina. Humans normally have three types of cones responding to different wavelengths. A different signal is applied by the different cone types, allowing perception of different colors. A typical cone cell forms a synapse with a neuron such as the bipolar cell. Intraocular device 60 is configured to drive the electrodes to directly stimulate different bipolar cells resulting in perception of different colors. Additionally or alternatively, the electrical charge driven by the electrodes into the retina is modulated such that different stimulation patterns are applied to the retina resulting in the perception of color (e.g., red, green and/or blue). Intraocular device 60 can then be calibrated based on the subject's input as to which stimulation pattern (typically based on varying pulse parameters) creates an optimal perception of color.

Additionally, photosensors 34 are color sensitive and configured to distinguish between certain colors (e.g., red, green and/or blue). Accordingly, electrodes 1064 are typically designated red, green and/or blue (by way of illustration and not limitation), corresponding to the colors sensed by photosensors 34. According to the sensing of different colors, the driving circuitry in intraocular device 60 drives electrical charges through the corresponding electrodes, resulting in the sensation of different colors (typically after an acclimation and/or training period).

Reference is still made to FIG. 8. For some applications, energy receiver 32 and voltage regulator 29 are isolated from photosensors 34, to reduce noise levels in intraocular device 60. Photosensors 34 are typically highly sensitive to energy levels of less than 1 pW, and are as a result susceptible to noise. Electrical stimulation by contrast creates relatively high power (0.1-1 uW) electrical signals, for neuron activation. Accordingly, noise generated by the high power signal is typically filtered from entering into the photosensing circuitry. Such filtering is typically implemented in the VLSI electrical design. Additionally, voltage regulator 29 is a main connection between the two circuits and to reduce noise transfer it is typically divided into two different circuits.

For some applications, power source 24 of the external device comprises an RF emitting power source. For such applications in which the power source comprises an RF emitting power source, an intraocular lens (IOL) is implanted in the eye of the subject, replacing the native lens. Typically, an RF receiving coil configured to receive RF energy emitted from the power source is incorporated into the IOL (configuration not shown). Incorporation of the RF receiving coil in the IOL, instead of implanting such a coil in a small epi-retinal space, generally enables the use of a large diameter RF receiving coil (e.g., 8-14 mm in diameter). Additionally, an RF receiving coil which is located in the IOL is in relative close proximity to the RF power source, enabling the use of a reduced amount of energy. Typically, the macula of the retina is spaced about 4-5 cm from eyeglasses 25 (eyeglasses 25 are shown in FIG. 1), which are coupled to an RF energy source. Thus the IOL with the RF receiving coil is positioned approximately 1.5-2 cm from the RF energy source. This enables higher RF efficiency than if an RF receiving coil were implanted in the retina. An intraocular unit comprising photosensors, driving circuitry and stimulating electrodes is typically implanted in either an epi-retinal or a sub-retinal location and configured to receive the energy from the RF receiving coil. For some applications, a wire transferring energy from the RF receiving coil to the intraocular unit extends between the RF receiving coil in the IOL and the intraocular unit.

Figure 9A:
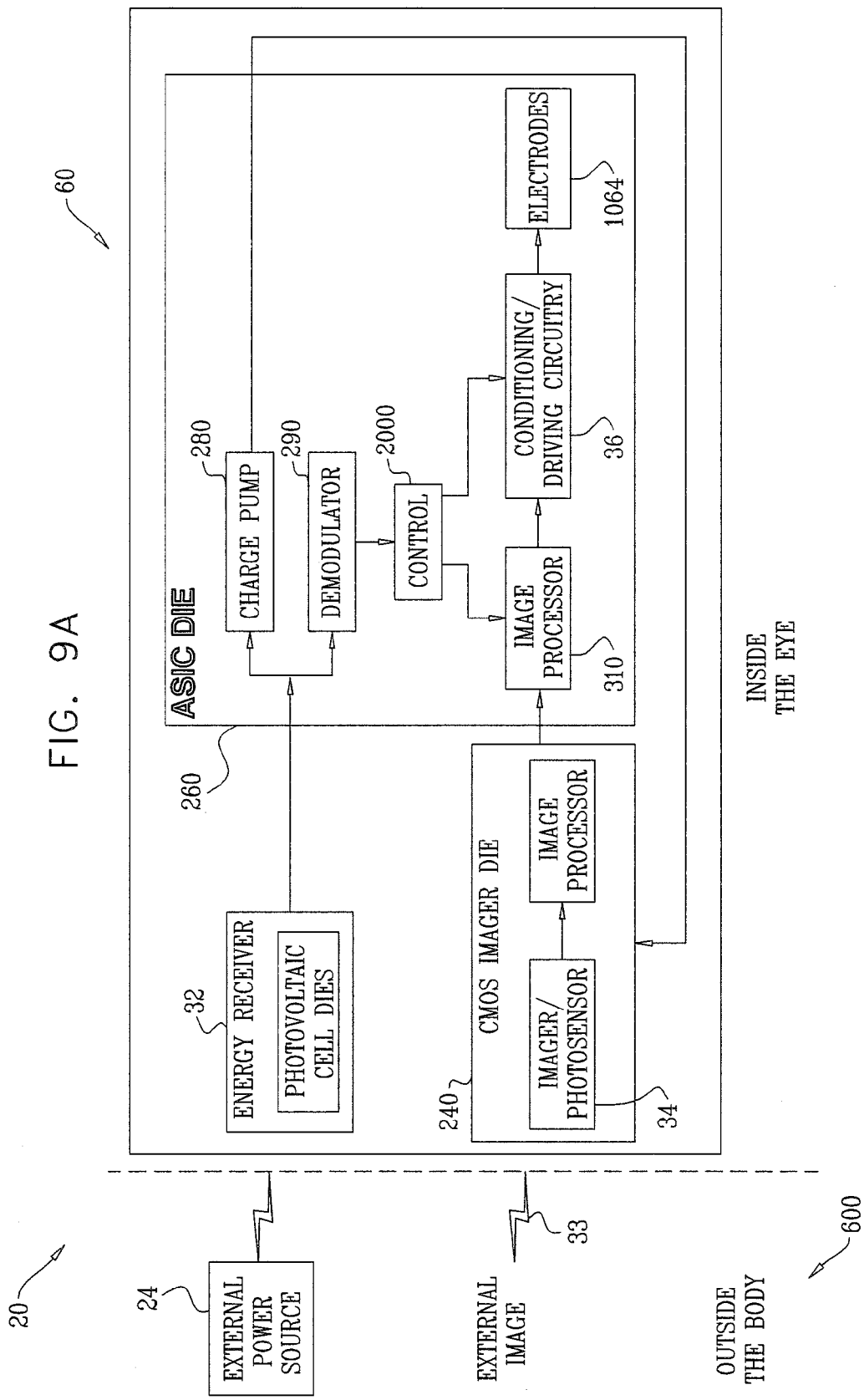
FIGS. 9A-C are schematic illustrations of the system for restoring vision, in accordance with some applications of the present invention.
Figure 9B:
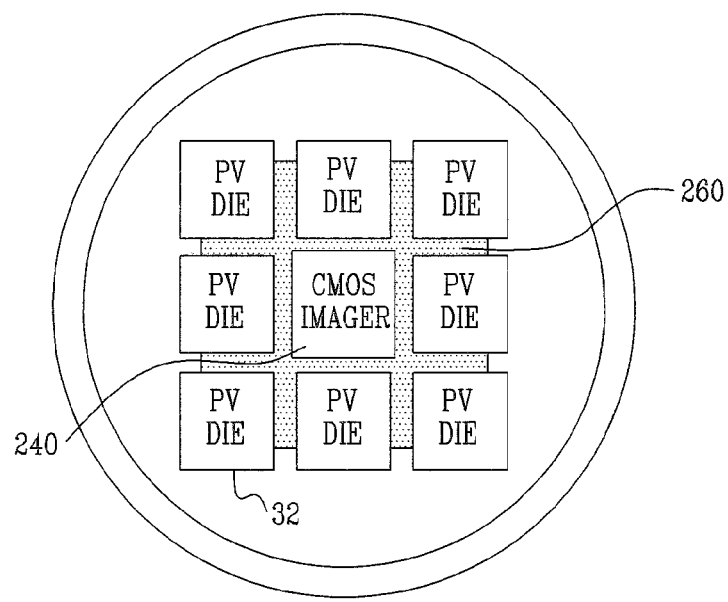
Figure 9C:
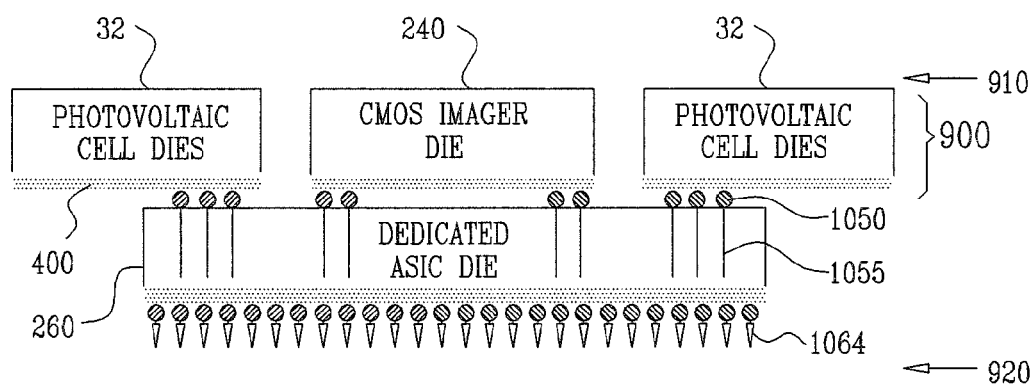

Reference is made to FIGS. 9A-C, which are schematic illustrations of system 20, in accordance with some applications of the present invention.

FIG. 9A is a block diagram of transmission of energy, information, and instructions, in the system for restoring vision, in accordance with some applications of the present invention. External device 600 is located outside of a body of a subject and comprises power source 24, which emits energy to power components of intraocular device 60. Intraocular device 60 is shown in FIG. 9A as comprising at least one energy receiving die 32, a CMOS imager die 240 and a custom-made ASIC die 260. The energy which is transmitted to device 60 is received by energy receiver 32, which typically comprises a plurality of discrete photovoltaic cell dies. Intraocular device 60 further comprises at least one array of photosensors 34, configured to detect photons 33 emanating from external objects and generate a photosensor signal responsively to the photons. Typically, the photosensors are incorporated into single CMOS imager die 240 comprising an imager and an image processor. This CMOS imager die may be similar to other low power CMOS imagers known in the art, and/or may be manufactured by companies such as Micron, OmniVision, ST, Mitsubishi and Kodak. For some applications, imager die 240 comprises between 10,000 and 5,000,000 pixels (by way of illustrations and not limitation). Typically, device 60 comprises between 1000 and 5000 stimulating electrodes.

The photosensor signal is transmitted to driving circuitry 36 which drives electrode 1064 to apply electrical charges to cells of the retina. As shown, for some applications, electrodes 1064 are coupled to a custom-made ASIC die 260. Typically, device 60 comprises a custom-made ASIC die 260 which additionally includes a charge pump 280, a demodulator 290, a control unit 2000, and an image processor 310. Energy from external power source 24 reaches energy receiver 32 and is passed via charge pump 280 to power components of intraocular device 60. The charge pump generates a higher voltage to be supplied to digital components of device 60. In addition to supplying power to components of ASIC die 260, charge pump 280 supplies power to imager die 240. Alternatively or additionally, photovoltaic cell dies of energy receiver 32 can be cascade wired, and thereby configured to increase voltage and enhance power supply to device 60. Energy from the energy receiver and charge pump is additionally passed to demodulator 290 and control unit 2000 in ASIC die 260. The demodulator typically receives modulated energy from energy receiver 32, and demodulates the energy to regulate, together with the control unit, operation of device 60 as described hereinabove with reference to FIG. 8. For other applications, software or hardware in the control unit is configured to demodulate the energy from energy receiver 32 to regulate operation of device 60 as described hereinabove. It is to be noted that techniques and apparatus described herein with reference to control unit 200 apply to control unit 2000 and vice versa, except where otherwise indicated.

ASIC die 260 further comprises an image processor 310 and is coupled to stimulating electrodes 1064 via driving circuitry 36 (including, for example, analog amplification functionality). The control unit typically regulates processing of the signal generated by photosensors 34 by image processor 310 in accordance with the now demodulated information. The processed photosensor signal is passed to driving circuitry 36, which drives stimulating electrodes 1064 to apply electrical charge to the retina of a subject.

For other applications, custom-made ASIC die 260 may, additionally to the above-mentioned components, also comprise energy receiver 32 and/or photosensors 34 or any combination thereof.

In an additional configuration, intraocular device 60 comprises custom-made ASIC die 260 and at least one photovoltaic die which comprises energy receiver 32 and photosensors 34.

Typically, ASIC die 260 comprises an integral BIT (built-in test), configured to generate an output when device 60 is implanted in an eye of a subject and transfer the output either in a wired or wireless manner, enabling calibration of device 60 after implantation. Alternatively, the output is used to calibrate device 60 prior to implantation, e.g., during manufacturing or pre-implantation processing.

Reference is now made to FIGS. 9B-C, which are schematic illustrations of a particular configuration of the components of device 60, in accordance with some applications of the present invention. FIGS. 9B-C show front and side views, respectively, of device 60 in accordance with some applications of the present invention. As shown, for some applications, the photosensors, which are configured to receive visible light, are incorporated into a single CMOS imager die. (Applications in which a plurality of CMOS imager dies are employed are not shown.) The CMOS imager die is typically surrounded by a plurality of photovoltaic dies configured to function as energy receivers 32 and receive energy from an external power source. Typically operation parameters of each photovoltaic die, e.g., the duration of an energy receiving period, is regulated by a discrete control unit coupled to each photovoltaic die. Alternatively, a central control unit regulates operation of the photovoltaic dies.

CMOS imager die 240 and energy receiving photovoltaic dies 32 are typically arranged in an array 900, which comprises the front side 910 of device 60 (the anterior side, when implanted). Typically, the imager die and the photovoltaic dies include a back side thereof, which forms the active surface 400 of these components. Solder bumps 1050 are deposited on a back side of array 900, electrically connecting array 900 to custom-made ASIC die 260 which typically includes through-silicon vias 1055. Alternatively the dies can be connected with wire bonding techniques. As shown in FIG. 9C, the ASIC die is coupled to electrodes 1064, which form the back side 920 of device 60 (the posterior side, when implanted). Typically device 60 is implanted in an eye of a subject, such that front side 910 of array 900 is facing the pupil, allowing visible light and energy from an external power source to strike array 900, and electrodes 1064 are positioned in a suitable orientation allowing the electrodes to directly contact and stimulate the tissue of the retina.

Figure 10:
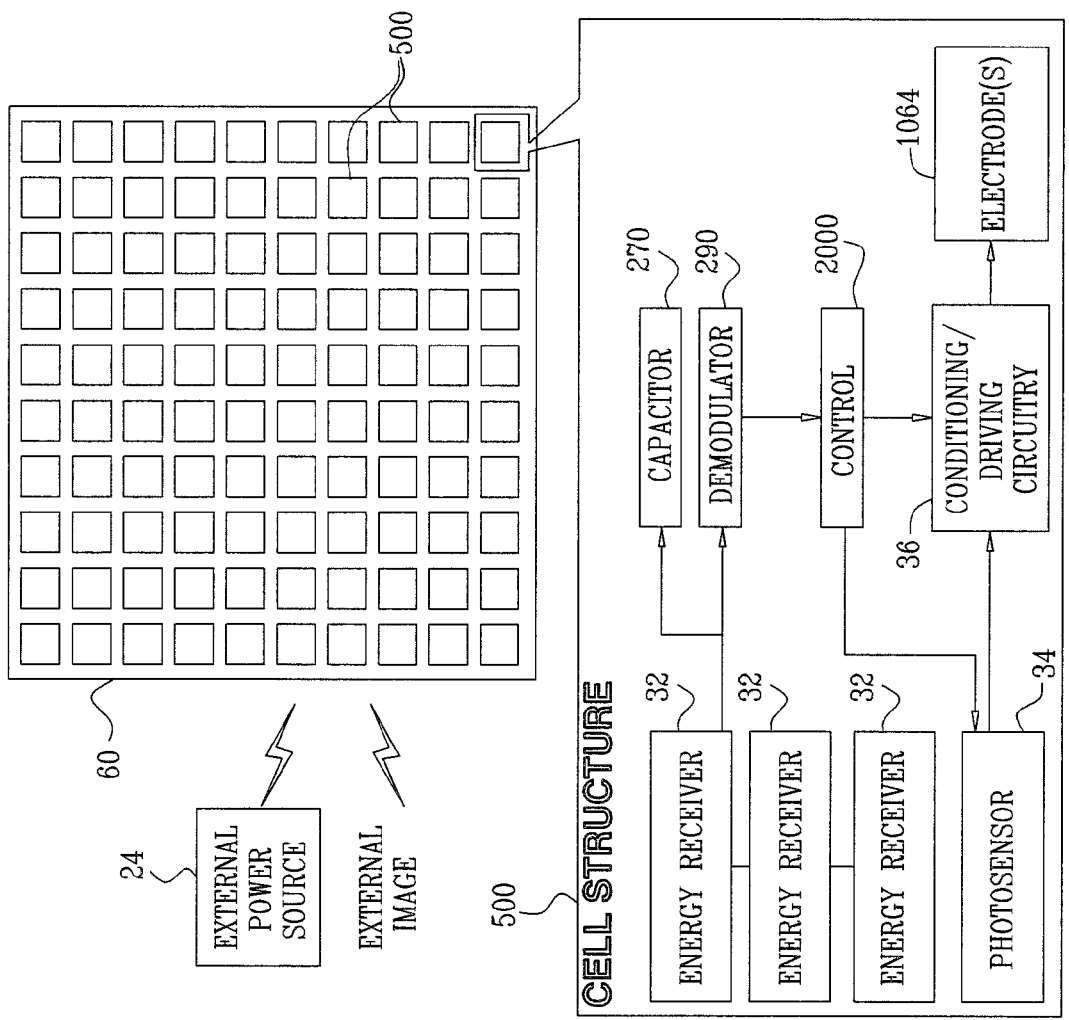
FIG. 10 is a block diagram of transmission of energy, information, and instructions, in the system for restoring vision, in accordance with some applications of the present invention.

Reference is made to FIG. 10, which is a block diagram of transmission of energy, information, and instructions, in the system for restoring vision, in accordance with some applications of the present invention. FIG. 10 shows an alternative configuration for intraocular device 60. In some applications, intraocular device 60 takes on a cellular-based configuration in which it comprises a plurality of cells, i.e., a plurality of the unit labeled 500. For some applications, intraocular device 60 comprises 1000-5000 such cells. Typically, each cell comprises an entire set of components including energy receivers 32, photosensors 34, a capacitor 270, a demodulator 290, a control unit 2000, driving circuitry 36 and 1-2 electrodes 1064. FIG. 10 shows a plurality of photovoltaic units which function as energy receivers 32 and receive energy from an external power source, e.g., a laser. For some applications, several photovoltaic units (shown in FIG. 10 as the three top photovoltaic units by way of illustration and not limitation) function as energy receivers 32, configured to receive energy from an external power source, e.g., a laser, to power the components of each cell 500. Additionally, for some applications, photosensors 34 (shown in FIG. 10 as the bottom unit by way of illustration and not limitation) are configured to receive photons emanating from an external object.

Figure 11A:
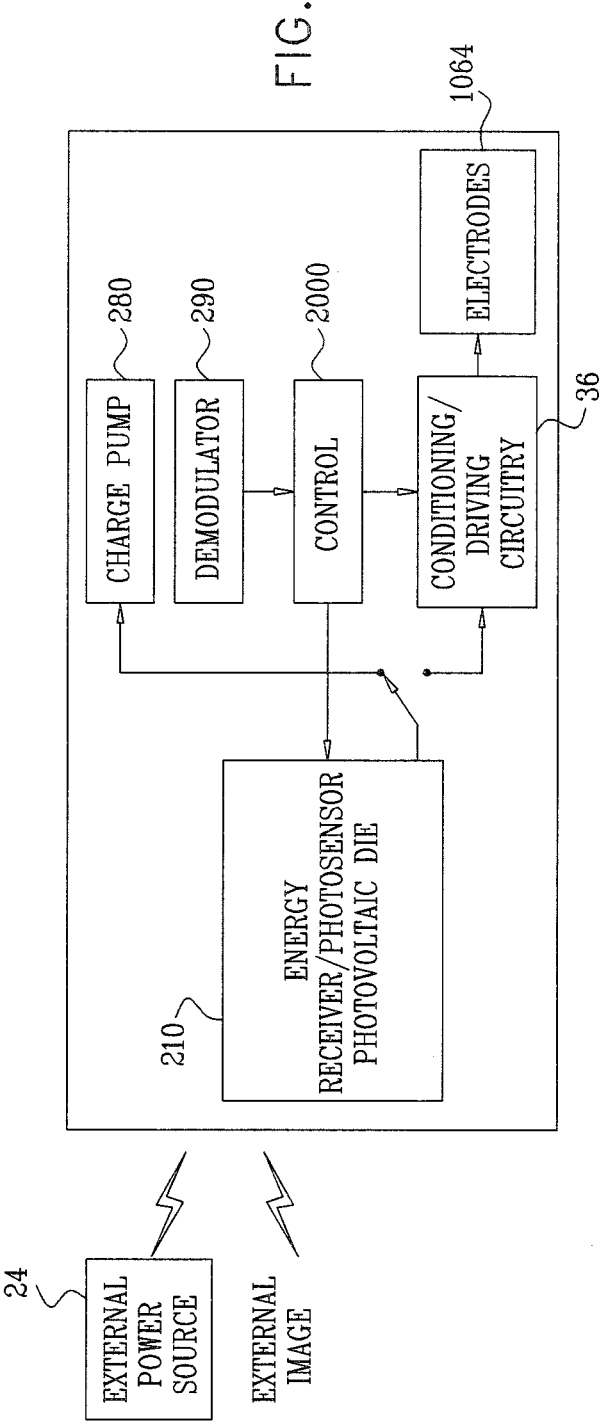
FIGS. 11A-B are block diagrams of transmission of energy, information, and instructions, in the system for restoring vision, in accordance with some applications of the present invention.
Figure 11B:
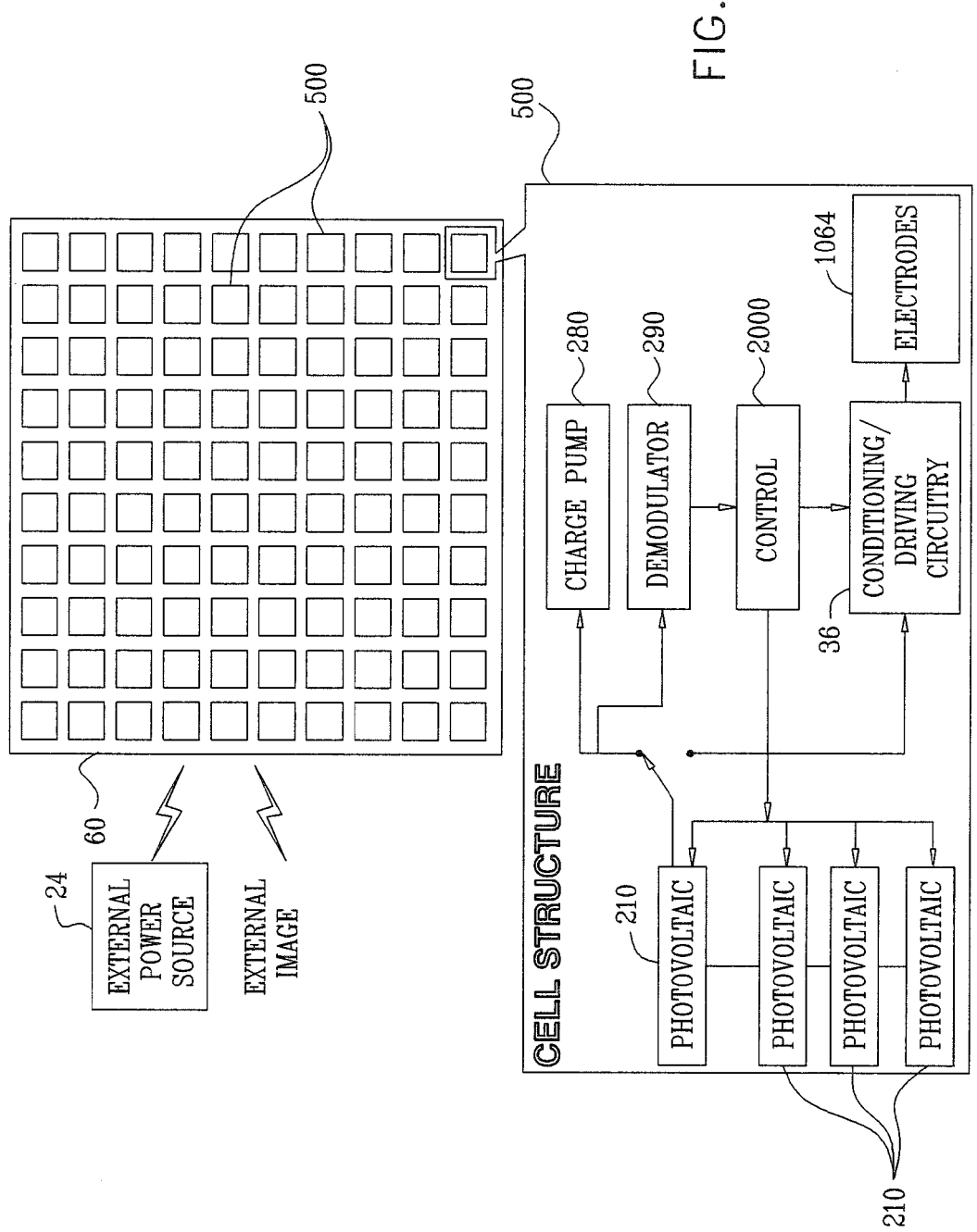

Reference is made to FIGS. 11A-B, which are block diagrams of transmission of energy, information, and instructions, in the system for restoring vision, in accordance with yet another application of the present invention. FIGS. 11A-B show external power source 24, which emits energy to power components of intraocular device 60. For some applications, a single light receiving element (indicated in FIG. 11A by box 210) functions, during alternating time periods, as an energy receiver, configured to receive energy from the external power source, and also as photosensors which are sensitive to visible light. FIG. 11A shows a central control unit 2000 which functions to regulate the operation of element 210 and to switch between energy receiving and photosensing. Central control unit 2000 further regulates the function of additional components of device 60 as described hereinabove. As shown for this application, device 60 further comprises a charge pump 280, a demodulator 290, an image processor 310 and stimulating electrodes 1064.

For some applications, intraocular device 60 comprises a plurality of fully functional cells 500 as described hereinabove with reference to FIG. 10. FIG. 11B shows a cell generally as described with reference to FIG. 10, with the distinction that each photovoltaic unit functions as both an energy receiver and a photosensor, during alternating time periods. FIG. 11B shows a plurality of light receiving elements 210 which function as energy receivers and photosensors, during alternating time periods. Typically, while functioning as an energy receiver, each component 210 receives energy to power device 60 from external power source 24. While functioning as photosensors, each element 210 is typically sensitive to ambient visible light which strikes components 210. As shown, for some applications, each cell 500 is regulated by a discrete control unit 2000 which is configured to regulate the operation of component 210 as an energy receiver and as a photosensor, during alternating time periods. Additionally, the control unit is configured to regulate switching of light receiving element 210 between energy receiving and photosensing. It is to be noted that for some applications element 210 is configured to receive other forms of energy, e.g., RF energy, to power components of intraocular device 60.

For some applications, the plurality of cells 500 are arranged in clusters of cells. Typically, the receiving of energy from the power source, and the receiving of visible light from an object, occur in two phases. For example, during a first phase, cells 500 in a cluster receive visible light and during a second phase receive energy from the power source, e.g., IR energy. The visible light received during the first phase is then used to define tissue stimulation during the second phase. Typically, the stimulation of each electrode in a given cluster occurs in sequence, in order to reduce short-term power requirements. Thus, for example, if there are four cells in a cluster, then during the second phase, each cell is actuated, in turn, to apply tissue stimulation in accordance with the light sensed by the photosensor of that cell.

Reference is made to FIGS. 9-11. Energy receivers 32 and/or photosensors 34 may comprise diodes selected from the group consisting of: a silicon diode, an amorphous silicon diode, a CMOS diode, a CMOS imaging 3-diode cell or a CMOS imaging 4-diode cell. Typically, any of these may be fabricated as back-illuminated energy receivers or photosensors, which allow passage of light through the substrate before striking the active surface. For such applications, fabrication techniques of back-illuminated sensors, which are described in one or more of the following references, are practiced in combination with techniques and device described herein: Swain et al., 2008 (referenced above) and http://www.sony.net/SonyInfo/News/Press/200806/08-069E/index.html.

Reference is made to FIGS. 1-11. For some applications, the electrodes described herein function to achieve biphasic stimulation of the cells. For example, the intraocular device may generate for example three voltages (e.g., 0 V, 1.5 V, and 3 V). A "ground" electrode is connected to the intermediate voltage, and a stimulation electrode is switched repeatedly between the higher voltage and the lower voltage, in order to produce biphasic stimulation. For some applications, a single voltage difference is generated (e.g., such that 0 V and 1.5 V are available) and this voltage difference is repeatedly switched to be in alternating electrical contact with two of the electrodes, so as to produce biphasic stimulation.

Reference is made to FIGS. 1-11. For some applications, a total volume V1 of the intraocular device is less than 0.2 cc.

The scope of the present invention includes embodiments described in the following patent applications, which is incorporated herein by reference. For some applications, techniques and apparatus described in the following patent application are combined with techniques and apparatus described herein:

U.S. patent application Ser. No. 12/368,150 to Gross, entitled, "Retinal Prosthesis," filed Feb. 9, 2009 which issued as U.S. Pat. No. 8,150,526 to Gross et al.

U.S. patent application Ser. No. 12/687,509 to Gefen, entitled, "Penetrating Electrodes for Retinal Stimulation," filed Jan. 14, 2010 which published as US 2011/0172736 to Gefen et al.

PCT Application PCT/1L2010/000097 to Gross entitled "Retinal Prosthesis," filed Feb. 3, 2010 which published as WO/2010/089739 to Gross et al.

For some applications, techniques described herein are practiced in combination with techniques described in one or more of the references cited in the Background section of the present patent application, which are incorporated herein by reference.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus configured for implantation in a body of a subject, comprising:
   an implantable array of at least 10 subsets of 3 or more electrodes; and
   for each subset, a respective power supply configured to provide current to the electrodes in the subset,
   wherein at least some of the electrodes in each subset are configured to drive respective electrical charges into tissue of the subject.

2. The apparatus according to claim 1, wherein the respective power supply for each subset comprises a common capacitor for the subset.

3. The apparatus according to claim 1, wherein the at least 10 subsets comprise 10-2500 subsets.

4. The apparatus according to claim 1, wherein a total volume of the apparatus is less than 0.2 cc.

5. The apparatus according to claim 1, wherein an electrode in at least one of the subsets is within 500 um of another electrode in the subset.

6. The apparatus according to claim 1, wherein an electrode in at least one of the subsets is within 300 um of another electrode in the subset.

7. Apparatus, comprising:
an external device, comprising:
- a mount, configured to be placed in front of an eye of a subject; and
- a power source coupled to the mount and configured to emit energy toward the eye; and an intraocular device configured to be implanted entirely in the subject's eye, the intraocular device comprising:
- a light receiving element configured to switch between:
  - a first time period, during which the light receiving element receives the energy from the power source and generates a voltage drop in response thereto; and
  - a second time period, during which the light receiving element detects photons and generates a signal in response thereto;
- a control unit configured to regulate the switch between the first and second time periods;
- a plurality of stimulating electrodes; and
- driving circuitry, coupled to the light receiving element, and configured to utilize the voltage drop to drive the electrodes to apply electrical charges to a retina of the eye in response to the signal from the light receiving element.

8. Apparatus configured for implantation in an eye of a subject, comprising:
an intraocular device comprising:
- a plurality of photosensors, each photosensor configured to detect photons and to generate a signal in response thereto;
- an array of at least 10 subsets of two or more electrodes; and
- a control unit, configured to drive at least some of the electrodes in each subset to non-simultaneously apply respective electrical charges into a retina of the subject, in response to photons detected generally simultaneously by respective ones of the photosensors.

9. The apparatus according to claim 8, wherein the control unit is configured such that the electrical charge driven by each electrode in a subset is returned via a plurality of the other electrodes in the subset.

10. The apparatus according to claim 8, wherein the control unit is configured such that the electrical charge driven by each electrode in a subset is returned via all of the other electrodes in the subset.

11. The apparatus according to claim 8, wherein the control unit is configured such that the electrical charge driven by each electrode in a subset is returned via an electrode in the subset that serves as a common return electrode for the other electrodes in the subset.

12. Apparatus, comprising:
an external device, comprising:
- a mount, configured to be placed in front of an eye of a subject; and
- a power source coupled to the mount and configured to emit energy toward the eye; and an intraocular device configured to be implanted entirely in the subject's eye, the intraocular device comprising a die comprising:
- an energy receiver, configured to receive the energy from the power source and to generate a voltage drop in response thereto; and
- a plurality of photosensors, each photosensor configured to detect photons and to generate a signal in response thereto, wherein the intraocular device further comprises an additional die, the additional die comprising:
- a plurality of stimulating electrodes; and
- driving circuitry, coupled to the energy receiver and to the photosensors, and configured to utilize the voltage drop to drive the electrodes to apply electrical charges to a retina of the eye in response to the signals from the photosensors, the additional die being sized such that the plurality of stimulating electrodes is configured to cover an area of the retina that is larger than an area of the plurality of photosensors.

13. The apparatus according to claim 12, wherein the die that comprises the energy receiver and the plurality of photosensors further comprises a charge pump configured to generate a voltage to be supplied to at least one component of the intraocular device.

14. The apparatus according to claim 12, wherein the external device is configured to modulate the energy emitted from the power source, and wherein the die that comprises the energy receiver and the plurality of photosensors comprises a control unit configured to demodulate the modulated energy and, in response, regulate an operation parameter of the intraocular device.

15. The apparatus according to claim 12, wherein the external device is configured to modulate the energy emitted from the power source, and wherein the die that comprises the energy receiver and the plurality of photosensors further comprises a demodulator configured to demodulate the modulated energy and, in response, regulate an operation parameter of the intraocular device.

16. The apparatus according to claim 12, wherein the additional die further comprises a charge pump configured to generate a voltage to be supplied to the intraocular device.

17. The apparatus according to claim 12, wherein the external device is configured to modulate the energy emitted from the power source, and wherein the additional die comprises a control unit configured to demodulate the modulated energy and, in response, regulate an operation parameter of the intraocular device.

18. The apparatus according to claim 12, wherein the external device is configured to modulate the energy emitted from the power source, and wherein the additional die further comprises a demodulator configured to demodulate the modulated energy and, in response, regulate an operation parameter of the intraocular device.

19. The apparatus according to claim 7, wherein the intraocular device further comprises a charge pump configured to generate a voltage to be supplied to at least one component of the intraocular device.

* * * * *